United States Patent
Dingeldein et al.

(10) Patent No.: US 8,652,645 B2
(45) Date of Patent: Feb. 18, 2014

(54) OSTEOSYNTHESIS WITH NANO-SILVER

(75) Inventors: Elvira Dingeldein, Dreieich (DE); Cyrille Gasqueres, Aschaffenburg (DE); Frank Witte, Hannover (DE); Amir Eliezer, Omer (IL)

(73) Assignee: aap Biomaterials GmbH, Dieburg (DE)

( * ) Notice: Subject to any disclaimer, the term of this patent is extended or adjusted under 35 U.S.C. 154(b) by 576 days.

(21) Appl. No.: 12/792,234

(22) Filed: Jun. 2, 2010

(65) Prior Publication Data

US 2010/0316686 A1 Dec. 16, 2010

Related U.S. Application Data

(60) Provisional application No. 61/183,261, filed on Jun. 2, 2009.

(30) Foreign Application Priority Data

Jun. 2, 2009 (DE) .......................... 10 2009 023 459

(51) Int. Cl.
- *B32B 15/04* (2006.01)
- *A61F 2/02* (2006.01)
- *C25D 11/00* (2006.01)

(52) U.S. Cl.
USPC ..... 428/472.1; 428/629; 428/701; 623/23.75; 623/23.76; 427/2.24

(58) Field of Classification Search
USPC ....................... 428/469, 472.1, 629, 701, 702; 623/11.11, 23.75, 23.76, 66.1; 427/2.24

See application file for complete search history.

(56) References Cited

U.S. PATENT DOCUMENTS

2005/0221259 A1* 10/2005 Anderson ................... 433/201.1
2006/0161256 A1* 7/2006 Ziegler et al. .............. 623/11.11

(Continued)

FOREIGN PATENT DOCUMENTS

| CN | 1276840 A | 12/2000 |
|----|-----------|---------|
| CN | 1367849 A | 9/2002 |

(Continued)

OTHER PUBLICATIONS

Nie et al., "Deposition of layered bioceramic hydroxyapatite/TiO2 coatings on titanium alloys using a hybrid technique of micro-arc oxidation and electrophoresis," 2000 (no month date), Elsevier, Surface and Coatings Technology, 125 (2000), pp. 407-414.*

(Continued)

*Primary Examiner* — David Sample
*Assistant Examiner* — Nicholas W Jordan
(74) *Attorney, Agent, or Firm* — Kaplan Breyer Schwarz & Ottesen, LLP

(57) ABSTRACT

The present invention relates generally to an antibacterial coating which is composed of silver, to medical tools and to implants comprising such a coating and to a method as well to an apparatus for the production of such a coating. The medical tools or the dental or orthopaedic implant comprises a metal or metal alloy having a treated surface wherein the treated surface is at least partially converted to an oxide film by plasma electrolytic oxidation using a colloid-dispersed system and wherein the converted surface is partially covered by islands formed by colloid-dispersed silver-particles of the colloid-dispersed system. An Ag—$TiO_2$ coating shows excellent properties in terms of antibacterial efficacy (even against multi-resistant strains), adhesion and biocompatibility. The life-time of an implant in a human body is increased. The antibacterial coating can be used in the field of traumatology, orthopaedic, osteosynthesis and/or endoprothesis, especially where high infection risk exists.

7 Claims, 24 Drawing Sheets

(56) References Cited

U.S. PATENT DOCUMENTS

2007/0259196 A1* 11/2007 Ruhle et al. .................. 428/540
2012/0024712 A1* 2/2012 Neumann et al. ............. 205/122

FOREIGN PATENT DOCUMENTS

| CN | 101054708 | 10/2007 |
|---|---|---|
| DE | 10 2008 008 517 A1 | 8/2009 |
| WO | 03094774 A1 | 11/2003 |
| WO | 2008045184 A1 | 4/2008 |
| WO | 2009053670 A2 | 4/2009 |
| WO | 2010139451 A2 | 12/2010 |

OTHER PUBLICATIONS

Lechner, Dr., "DE Application No. 10 2009 023 459.4 Office Action Dec. 21, 2011",, Publisher: DPMA, Published in: DE.

Dr. Lechner, "German Office action for Application No. 10 2009 023 459.4-45", Feb. 11, 2010, Publisher: German Patent Office, Published in: Germany.

Duszczyk, Jurek, "Protest letter—email 1".
Witte, Frank, "Re: protest letter—email 1".
Witte, Frank, "Email—Dec. 23, 2008".
Duszczyk, Jurek, "Protest letter—email 2".
Duszczyk, Jurek, "Protest letter—email 3".
Necula et al., "Enrichment of anodic MgO layers with Ag nanoparticles for biomedical applications", "Journal of Materials Science: Materials in Medicine", 2009, pp. 339-345, Publisher: Springer.
Necula et al., "In vitro antibacterial activity of porous $TiO_2$—Ag composite layers against methicillin-resistant *Staphylococcus aureus*", "Acta Biomaterialia", 2009, pp. 3573-3580, No. 5, Publisher: Elsevier Ltd.
Duszczyk, Jurek, "Protest letter".
Duszczyk, Jurek, "Protest letter—corrected".
Witte, Frank, "Re: Protest letter".
"Related Chinese Patent Application No. I: 2010 80029470.0 Office Action", Sep. 29, 2013, Publisher: CIPO, Published in: CN.

* cited by examiner

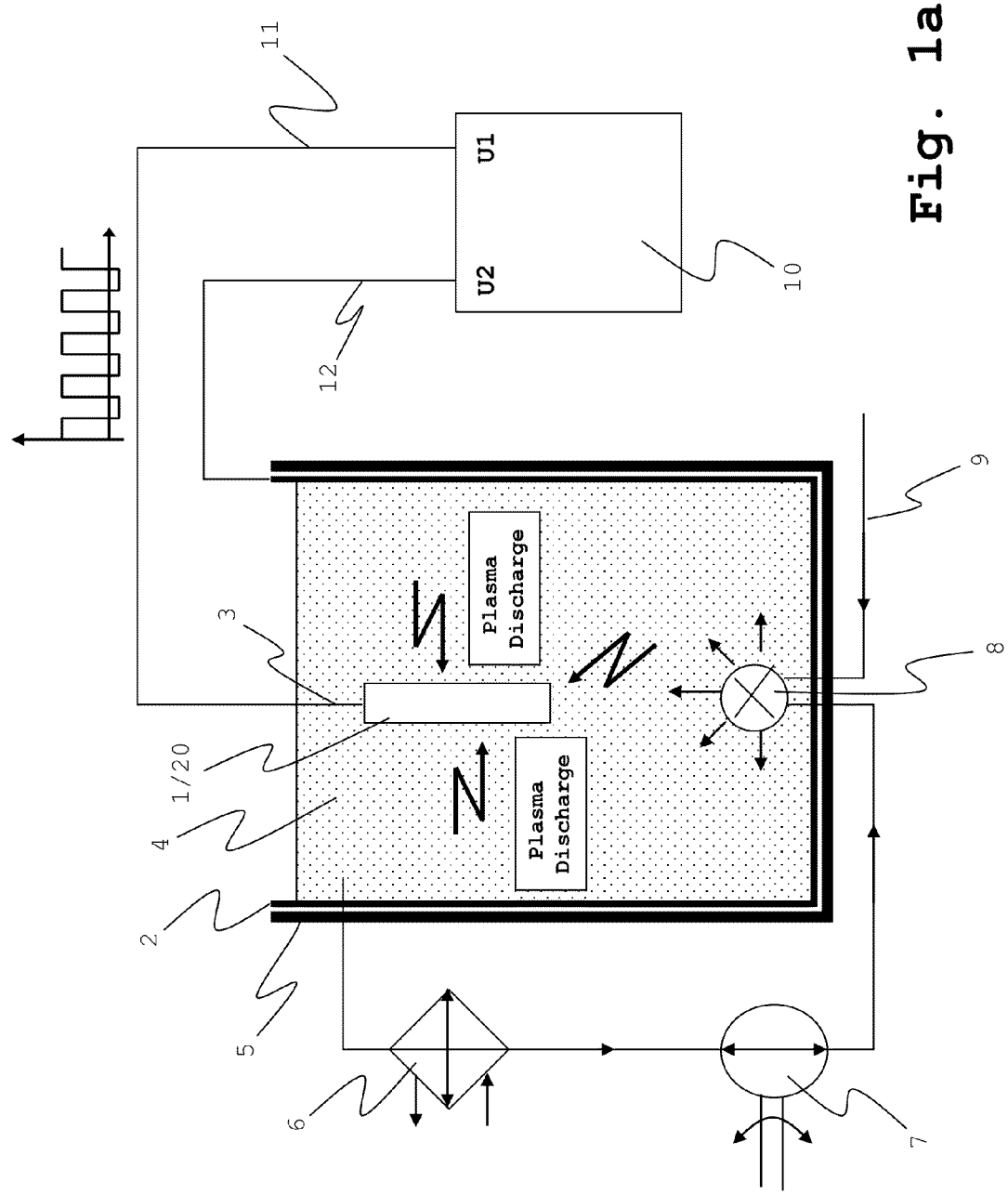

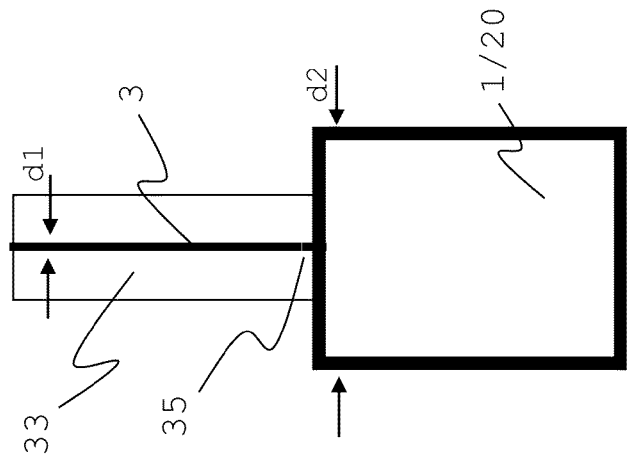
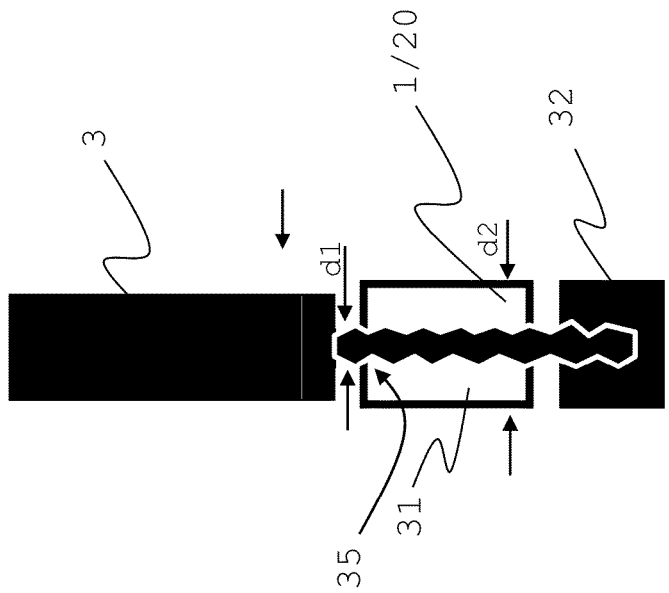
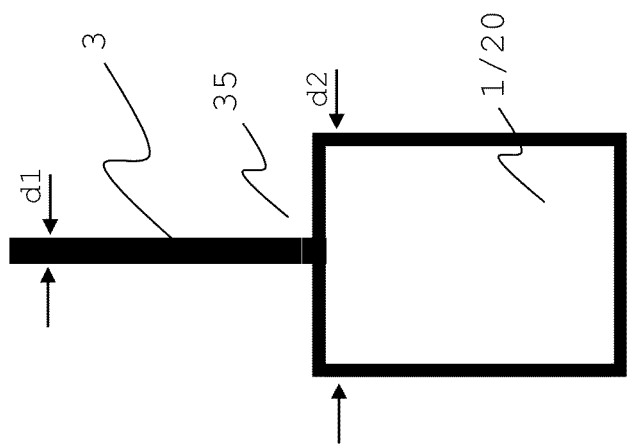
Fig. 1b
Fig. 1c
Fig. 1d

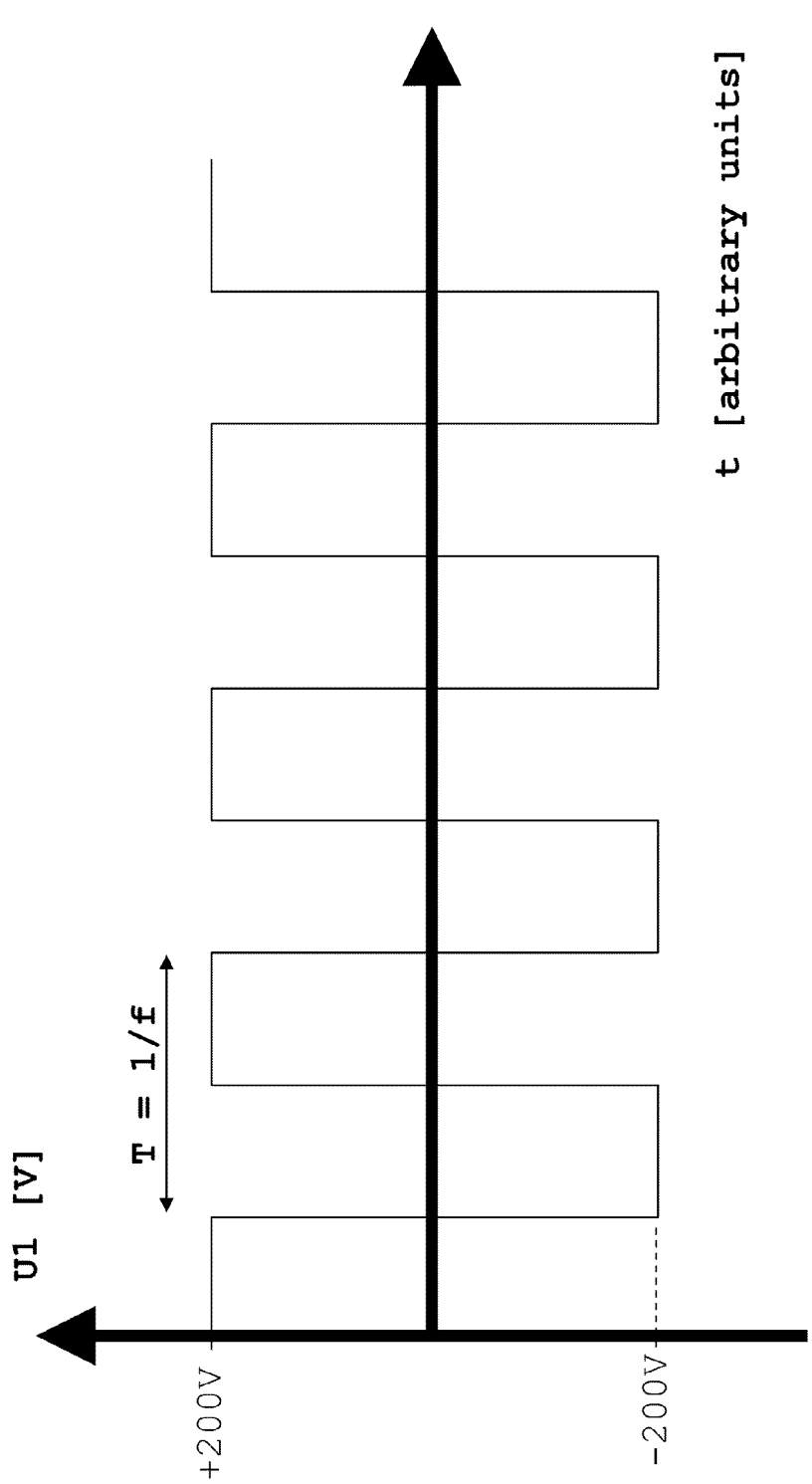

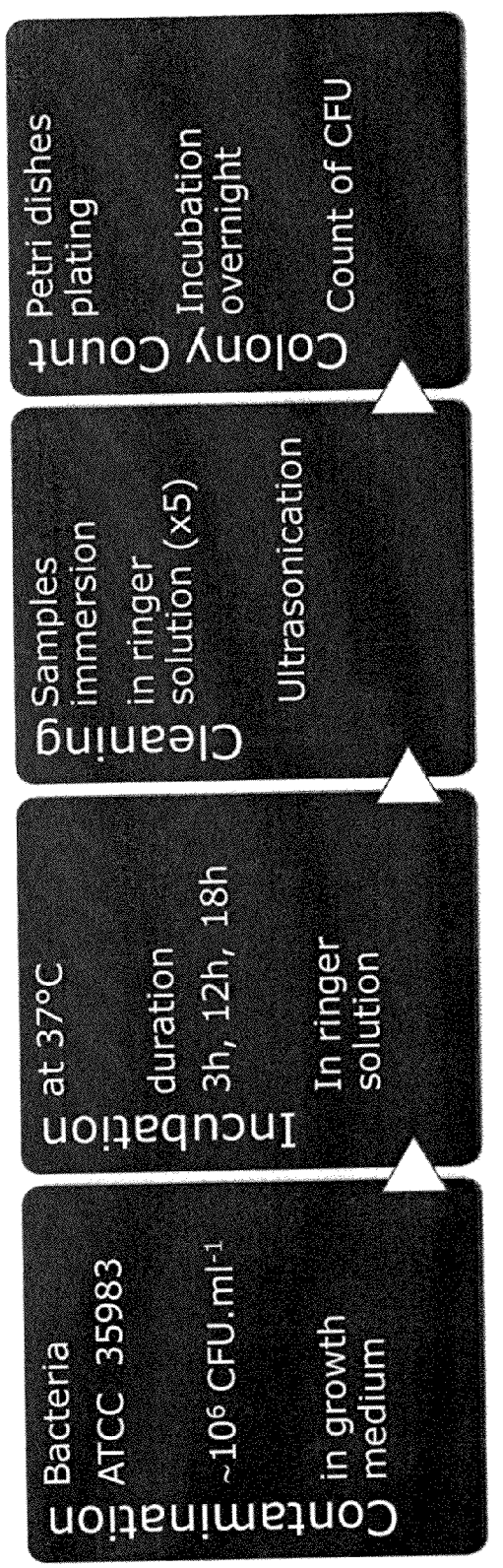
Fig. 5.a

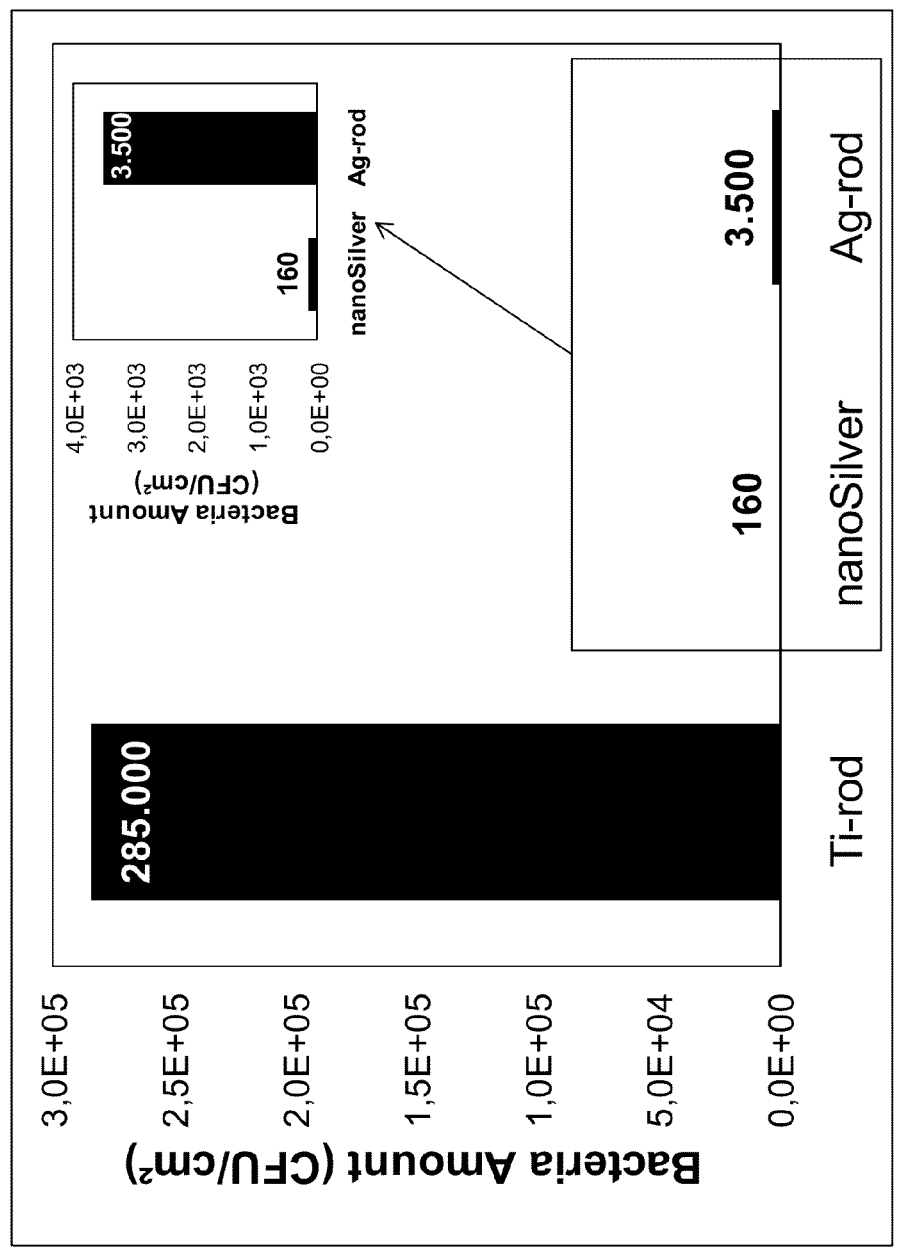
Fig. 5.b

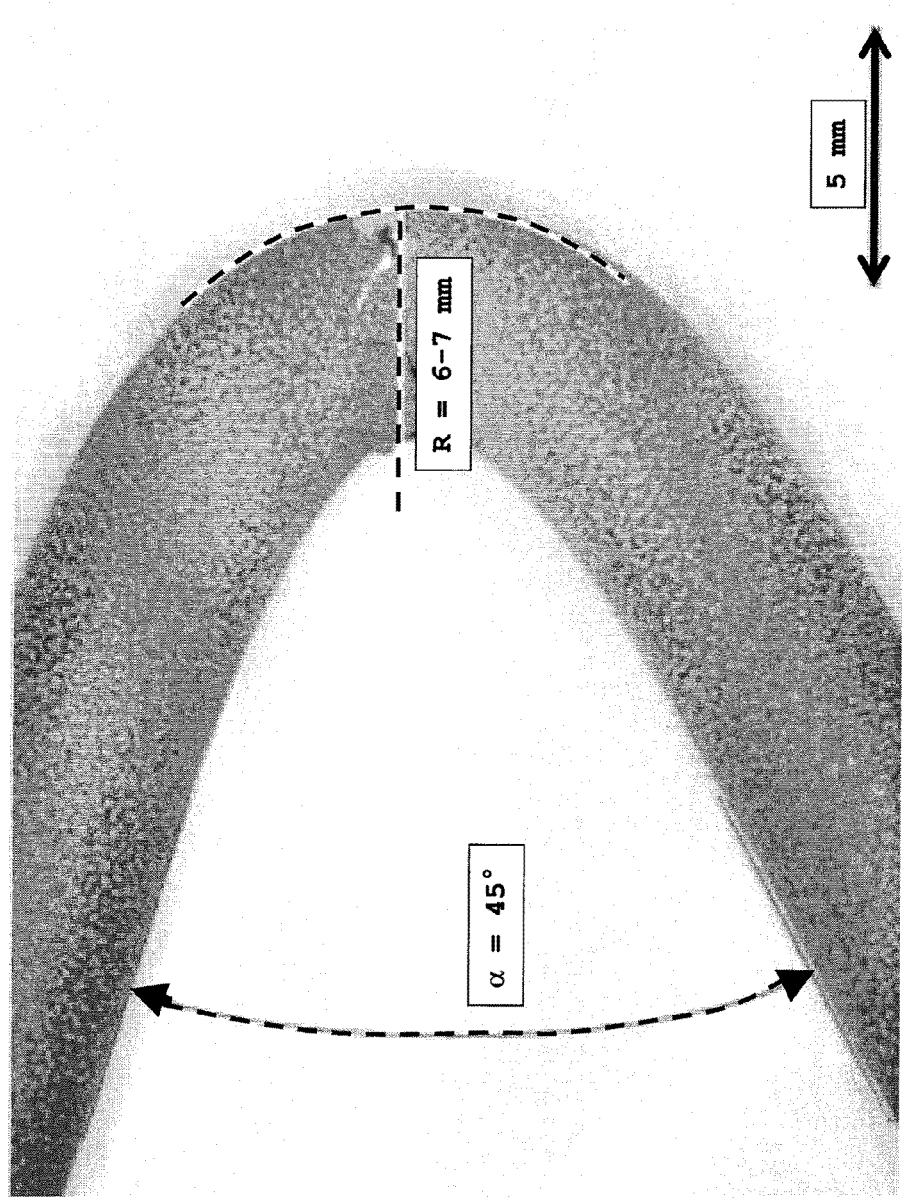

OSTEOSYNTHESIS WITH NANO-SILVER

CROSS-REFERENCE TO RELATED APPLICATIONS

U.S. patent application No. 61/183,261 and German Patent application No. 10 2009 023 459.4, both filed on Jun. 2, 2009, are incorporated herein by reference.

FIELD OF THE INVENTION

The present invention relates generally to a multifunctional antibacterial coating which is composed of silver, to implants and/or to medical tools comprising such a coating and to a method as well to an apparatus for the production of such a coating.

BACKGROUND OF THE INVENTION

It is known that silver ions strongly inhibit the growth of bacteria and other microorganisms. Silver ions destroy important cell components of microorganisms, so that their vital functions do not work anymore. Silver shows a broad-spectrum antibacterial activity and is even efficient against antibiotic-resistant strains. Moreover, silver targets numerous sites within the bacterial cell, thus decreasing the chance for the bacteria to develop any kind of resistance.

With increasing resistance of most of the pathogen germs against the usually used antibiotics, silver was recently rediscovered as an antibacterial active substance. In fact, due to its disinfectant property, silver has long been used for hygienic and medicinal purposes.

For instance, silver compounds were major weapons against wound infection in World War I until the advent of antibiotics. In 1884 German obstetrician C.S.F. Crede introduced 1% silver nitrate as an eye solution for prevention of Gonococcal ophthalmia neonatorum, which is perhaps the first scientifically documented medical use of silver. Further, silver sulfadiazine cream was a standard antibacterial treatment for serious burn wounds and is still widely used in burns units.

Currently, many silver containing products are available on the market such as wound dressings, catheters and/or tumor prosthetic systems.

One known coating fabrication method is based on a vacuum coating method which offers reliable protection for the surfaces of medical implants against bacterial contamination. A pure silver coating is applied via a PVD (Physical Vapor Deposition) process followed by a silicon oxide coating deposited via a PECVD (Plasma Enhanced Chemical Vapor Deposition) process. The coating thickness is generally below 200 nm.

PVD and CVD processes usually require highly expensive coating systems. Further, they are also energy consuming due to the high vacuum requirements. Furthermore, the PVD technique is a "line-of-sight" technique, which means that complex surfaces would be very hard to coat homogeneously.

Moreover, irreversible pigmentation of the skin and/or the eye, i.e. argyria or argyrosis, due to possible "excessive" silver deposition, may develop after prolonged exposure to silver or silver compounds.

Besides, leukopenias and neuromuscular damages could be caused by increased silver concentrations. Allergic reactions were described in the literature. Past coating attempts with silver salts or elementary silver were reported to cause significant increases of silver concentrations in the serum of the concerned patients.

Accordingly, it is an object of the present invention to provide a medical device, for instance embodied as an implant, having a coating of advanced properties.

Preferably such a coating should be provided as an antibacterial coating, for instance on metallic implants.

In particular it should be possible to control or to adapt the antibacterial efficacy, for instance the leaching rate, of such a coating.

Preferably the ingrowth of human tissue and/or bone should be promoted by such a coating on an implant.

The fabrication of such a coating should be based on an easy and cost reduced concept.

SUMMARY OF THE INVENTION

Accordingly, the invention proposes a method for treating a surface of a medical device, in particular a metallic medical device, preferably of a non-biodegradable material, comprising the following steps:
providing a colloid-dispersed system,
subjecting a medical device to the colloid-dispersed system such that a surface of the medical device which is to be treated is immersed in the colloid-dispersed system,
generating a, preferably asymmetric or symmetric or a combination of both asymmetric and symmetric, AC voltage difference between the medical device as a first electrode and/or a second electrode positioned in the colloid-dispersed system
to convert the immersed surface to an oxide film by plasma electrolytic oxidation wherein the converted surface is partially covered by islands formed by colloid-dispersed particles of the colloid-dispersed system.

The invention also proposes a medical device comprising a, preferably non-biodegradable, metal or metal alloy having a treated surface wherein
the treated surface is at least partially converted to an oxide film by plasma electrolytic oxidation using a colloid-dispersed system and wherein
the converted surface is partially covered by islands formed by colloid-dispersed particles of the colloid-dispersed system.

A porous oxide film or layer is grown by the plasma electrolytic oxidation (PEO) process. By the PEO process, the metallic substrate is provided as the first electrode, preferably as an anode, in an "electrolytic cell". Its surface is converted into the corresponding metal oxide under the applied electrical field. The oxide film consists of crystalline phases, with a highly porous surface and with components derived from both the colloid-dispersed system and the medical device, for instance an implant, as a substrate. It is provided a synthesis of a metal-oxide-particle-nanocomposite-coatings by in situ deposition. The particles are applied onto the surface of the medical device when oxidizing the medical device surface. The present invention enables the formation of a coating onto any type of shape of a medical device.

The colloid-dispersed system also can be called dispersion. It is a liquid containing dispersed particles, in particular the colloid-dispersed-particles. The colloid-dispersed-particles have a mean average diameter of less than or equal to 100 nm, preferably less than or equal to 50 nm, most preferably less than or equal to 30 nm. The particles are also named as nano-particles. The particles are dispersed and not dissolved in the colloid-dispersed system.

Preferably the particles are not provided as a powder having generally a broad size distribution. In a preferred embodiment the particles have a narrow size distribution with a FWHM (full width at half maximum) of ≤25 nm. Such a size distribution enables the formation of uniform islands and an improved conductivity in the dispersion.

In one preferred embodiment the particles are provided by silver-particles (Ag-particles or Ag-nano-particles). Such a nanoSilver coating on medical device surface, for instance an implant surfaces, shows several beneficial effects: a reduction of bacterial adhesion, and an inhibition of bacterial growth. So far, no resistance mechanism was reported and detected against silver effect. Since silver acts more like an antiseptic than an antibiotic. Such a nanoSilver coating shows excellent properties in terms of antibacterial efficacy (even against multi-resistant strains), adhesion and biocompatibility (for further benefits see the detailed description of the invention). This nanoSilver containing layer is provided by a surface chemical conversion of the implant induced by means of the plasma electrolytic oxidation.

As a supplement or as an alternative, the particles are provided by apatite-particles, preferably HA-particles (hydroxyapatite). The apatite is at least one apatite selected from a group consisting of hydroxyapatite, Si-substituted hydroxyapatite, flourapatite and carbonated apatites. At least one Ca-atom of an apatite can be replaced by a Mg, Zn, Cu, Na, K and Sr.

Hydroxyapatite improves osteoconduction. This enables for instance a strong fixation of an implant inserted in a human or animal body. The HA-particles according to the invention also cover HA-Si-compounds (Si-substituted hydroxyapatite). A HA-Si-compound is HA-compound in which at least one $PO_4^{3-}$ group is replaced by a $SiO_4^{3-}$ group. Such a HA-Si-compound is characterized by an enhanced bio-compatibility.

As a further supplement or as a further alternative, the particles are provided by at least one type of particles selected from a group consisting of copper and zinc. This type of particles also shows an antibacterial effect.

In a further embodiment an additive, preferably a nano-sized additive, is provided in the dispersion. Accordingly, the particles comprise an additive wherein the additive is at least one material selected from a group consisting of metals, oxides, earth minerals and phosphates. Some typical examples are magnesia, calcium phosphate, α-TCP (tri-calcium-phosphate), sodium water glass, potassium water glass and/or silicon. Glass water is effective in bone mineralization. The additive is dissolved or dispersed in the colloid-dispersed system. It is emphasized that above mentioned additives are exemplary and not restricted to this enumeration.

The colloid-dispersed system can be based on any kind of liquid, in particular of low or zero conductivity. In one embodiment the colloid-dispersed system is provided as a water-based dispersion. Preferably the dispersion means are pure water or ion-exchanged water. The used water essentially comprises no electrolytes. In a preferred embodiment intentionally no additional electrolytes are introduced in the distilled water. The ph-value of the used water is less than or equal to 7 or the ph-value of the used water is less than or equal to 7.4.

The particles as the dispersed phase of the dispersion are provided with a concentration of less than or equal to 100 mg/l, preferably less than or equal to 20 mg/l, most preferably less than or equal to 2 mg/l. In the most preferred embodiment the concentration is less than or equal to 2 mg/l. This value is in particular suitable for metallic particles, in particular for Ag-particles to avoid cytotoxic effects. Moreover, these values are in particular suitable for metallic particles, in particular Ag-particles, to provide a sufficient conductivity in the colloid-dispersed system.

In a preferred embodiment the conductivity in the colloid-dispersed system is essentially only or only provided by the colloid-dispersed-particles themselves. This is in particular suitable for metallic particles, as for instance Ag-particles, in particular in combination with an emulsifier. Preferably the particles, for instance Ag-nano-particles, are the only carrier or the most active carrier for the electrical charge in the dispersion. In a preferred embodiment the particles or metallic particles are provided by a material, forming the islands on the oxide film. One material example represents silver. As a supplement or as an alternative the metallic particles or the dispersed metallic particles are provided by a component which is a component of the substrate material. For instance the particles are provided by Ti-particles if the substrate (representing the medical device) comprises titanium. A contamination can be avoided. Also dissolved material, as for instance dissolved material of an immersed medical device, can contribute to the conductivity in the colloid-dispersed system.

As an alternative or as a supplement at least one electrolyte is provided in the colloid-dispersed system. The electrolyte is dissolved in the colloid-dispersed system. In one embodiment the electrolyte comprises at least one material selected from a group consisting of metals, oxides, earth minerals and phosphates. In another embodiment the electrolyte comprises at least one electrolyte selected from a component of the substrate material. I.e. the electrolyte is adapted to the substrate material. For instance the electrolyte is provided by Ti-ions if the substrate (representing the implant) comprises titanium. A contamination can be avoided. It is emphasized that above mentioned electrolytes are exemplary and not restricted to this enumeration.

In a further embodiment a gas is provided in the colloid-dispersed system. The gas is for instance provided by a kind of bubbling. Particularly the gas is provided such to influence the PEO and/or to participate in the PEO. The gas comprises at least one type of gas selected from a group consisting of $N_2$, Ar, Kr and Xe. The mentioned noble gases are in particular suitable to achieve an enhanced densification of the converted layer.

The converted medical device surface, for instance the converted implant surface, is uniformly covered with the oxide layer. Preferably the converted surface is continuously covered with the oxide layer. The oxide film has a thickness of 1 μm to 100 μm, preferably 10 μm to 100 μm, most preferably of 20 μm to 40 μm. The oxide film is characterized by hills and/or plateaus separated by grooves and/or channels. Such an appearance represents a typical feature of a PEO process. Such a structure results in a medical device surface or implant surface of large specific surface area.

As already stated in the preceding description the particles are applied onto the surface of the medical device when oxidizing the medical device surface. A small fraction of the particles are also embedded in the oxide layer. The main fraction of the particles is deposited onto the surface of the oxide layer forming the islands.

There exists no sharp interface between the oxide layer and the deposited particle layer. The particle concentration in the surface converted medical device, for instance the surface converted implant, is decreasing, preferably continuously decreasing, with increasing depth.

The islands are provided by means of micro-arcs in the PEO process, for instance by implantation and/or deposition and/or agglomeration of the dispersed particles. The islands are surrounded by the oxide layer. The islands have a typical average-size of less than 300 nm. An average thickness is in the range of 1 nm to 1000 nm, preferably in the range of 5 nm to 400 nm. Some islands also can be connected to each other.

Typically, there is essentially no or only few porosity in the islands, in particular forming nano-areas.

However, the islands represent a non-continuous layer or film, for instance of silver, on the oxide film. In one embodiment the medical device surface is a TiO—Ag-nano-composite-coating. Accordingly, the elements or compounds Ti, $TiO_2$, Ag and AgO are directly "visible" respectively detectable on the surface. The treated surface has an average island cover amount of below or equal to 20%, preferably below or equal to 10%.

A chemical characterization of a treated surface results in a composition of colloid-dispersed-particles, preferably silver, of 0.5 to 10 at. %, preferably 1 to 10 at. % most preferably 2 to 6 at. %.

The chemical characterization of nano-silver on titanium or on a titanium alloy results in the following composition:

|       | Ag   | Ti   | Al  | V   | O     |
|-------|------|------|-----|-----|-------|
| at. % | 1-10 | 5-40 | 0-5 | 0-2 | 30-70 |

The controlling of the covering amount of the islands can be used to adjust the "effect" of the islands. For instance the antibacterial efficacy can be adjusted. One parameter for the antibacterial efficacy represents the leaching rate for instance of silver ions.

In the embodiment of Ag-particles the treated surface has an Ag ions leaching rate of less than 120 $ng \cdot cm^{-2} \cdot day^{-1}$. A surface treatment with silver respectively nanoSilver shows a very high antimicrobial efficacy with very small potential side effects. Due to the high surface on volume ratio of nanoparticles (size preferably between 2 and 50 nm), a high efficiency is expected even at small doses, thus, reducing the risk of noxious effect on cells.

The AC voltage or alternating voltage is applied to the first electrode and/or the second electrode. The AC voltage is provided with a frequency of 0.01 Hz to 1200 Hz.

In a preferred embodiment the AC voltage is provided as an asymmetric AC voltage. The asymmetric AC voltage difference or asymmetric AC voltage represents an unbalanced AC voltage. This is an alternating voltage with different amplitudes to the negative and the positive components. It is emphasized that a pulsed DC voltage can be also interpreted as the AC voltage. The negative component is provided with an amplitude ranging from −1200 V to −0.1 V. Preferably, the negative component is provided with an amplitude ranging from −350 V to −0.1 V. In one embodiment, the negative component is provided with an amplitude below −180 V or ranging from −350 V to −180 V. The positive component is provided with an amplitude ranging from 0.1 V to 4800 V. Preferably, the positive component is provided with an amplitude ranging from 0.1 V to 1400 V. In one embodiment, the positive component is provided with an amplitude above +250 V or ranging from +250 V to 1400 V. In particular the quotient of the positive amplitude divided by the negative amplitude needs to be adjusted. The absolute value of the quotient ranges from larger 1 to 4.

In another embodiment the AC voltage is provided as a symmetric AC voltage. The negative component of the AC voltage is provided with an amplitude ranging from −2400 V to −0.1 V. Preferably, the negative component is provided with an amplitude ranging from −1200 V to −0.1 V. The positive component of the AC voltage is provided with an amplitude ranging from +0.1 V to +2400 V. Preferably, the positive component is provided with an amplitude ranging from 0.1 V to 1200V.

A combination of both an asymmetric and a symmetric AC voltage is also possible. Such a voltage distribution is for instance suitable for a step-by-step-process or a multi-step-process for the fabrication of one coating. In a first step an asymmetric voltage or a symmetric voltage is applied to form the coating. In a further or second step, in particular after an interruption, the formation of the coating is continued by the application of a symmetric voltage or an asymmetric voltage respectively.

The voltage difference is provided with a magnitude which is sufficient for carrying out PEO. The voltage is above a breakdown voltage of the oxide film growing on the surface of the implant. Preferably the maximum of the AC voltage difference is provided in the range of 0.1 V to 4800 V. Most preferably the maximum of the AC voltage difference is provided in the range of 100 V to 1400 V. In dependence on the conductivity of the colloid-dispersed system and an optional additional electrolyte, the applied voltage difference results to a current density of 0.00001 to 500 $A/dm^2$, preferably of 0.00001 to 100 $A/dm^2$. Preferably, the applied voltage or voltage distribution is essentially constant or unchanged and the current density is adjusted during the PEO process.

A deposition rate in the range of 0.01 μm/s to 1 μm/s is achieved. Accordingly, with respect to the advantageous thickness of the oxide layer and/or the particles islands a deposition time in the range of 1 s to 1200 s, preferred 1 s to 300 s, most preferred 20 s to 260 s, is achievable.

To enable a stable dispersion, the colloid-dispersed system is provided with a temperature of −20° C. to +150° C., preferably −20° C. to +100° C., most preferably between 0° C. to 75° C. The colloid-dispersed system is circulated with a circulation rate of 0 to 5000 liter/min, preferably 0.01 to 500 liter/min. This is for instance achieved by a mixer or mixing means or stirring means. As an optional supplement an emulsifying agent or emulsifier is provided in the colloid-dispersed system, in particular to avoid or to reduce an agglomeration of particles. A typical volume of the colloid-dispersed system is in the order of 0.001 liter to 500 liter, preferably 0.1 liter to 500 liter, most preferably 3 to 20 liter. Such volumes support an improved electrical field distribution in the dispersed system.

An initial medical device surface without any polishing is sufficient to achieve a suitable uniform converted surface and a suitable stable bonding of the converted surface to the bulk material. The initial surface describes the surface before subjecting the medical device to the PEO process. A mechanically polishing of the initial surface is sufficient to achieve enhanced properties. A cost-intensive electro-polishing resulting in a very smooth surface is not necessary.

The invention also proposes an apparatus for the treatment of a surface of a medical device, in particular a metallic medical device, by plasma electrolytic oxidation comprising following components:
  a bath for containing a colloid-dispersed system,
  preferably means for mixing a colloid-dispersed system in the bath,
  means for holding a medical device such that a surface of a medical device which is to be treated is immersed in a colloid-dispersed system wherein a medical device provides a first electrode,
  means for providing a second electrode in a colloid-dispersed system contained in the bath, a power supply unit for generating an AC voltage which is supplied to the first electrode and/or the second electrode, means for connecting the first electrode and/or the second electrode to the power supply unit wherein the means for connecting the first electrode are adapted to an immersed medical device such that the cross section ratio ranges from 0.1 to 10. Preferably, the cross section ratio ranges from 0.75 to 4.

The cross section ratio represents the quotient of the medical device cross section divided by the cross section of the means for connecting the first electrode. The adapted ratio is particularly determined in the vicinity of the interface between the medical device and the means for connecting.

Preferably the means for connecting the first electrode are embodied to provide an essentially uniform electric field distribution between the first electrode and the second electrode, in particular in the vicinity of the treated surface of the medical device.

A uniform electric field distribution between the first electrode and the second electrode is advantageous to achieve a surface conversion of enhanced uniformity. The inventors surprisingly discovered that the electric field distribution between the first electrode and the second electrode is strongly influenced by the embodiment of the means for connecting the first electrode. In detail, the electric field distribution is strongly dependent on the design and/or the dimensions of the means for connecting the first electrode.

The required uniform electric field distribution is achieved by means for connecting the first electrode having an adapted reduced or an adapted increased cross section with respect to the cross section of the connected medical device. In one embodiment the means for connecting the first electrode have a, preferably circular, cross section with an average diameter of less than or equal to 5 mm, preferably less than or equal to 1.5 mm. In a preferred embodiment the means for connecting the first electrode are provided as a wire. The wire is metallic. The wire is embodied to carry an electric current and is for instance embodied as a thread, a rod or a strand. The wire can be flexible or non-flexible. The means for connecting the first electrode are fixed to the medical device as the first electrode. The means for connecting the first electrode, in particular the wire, can be fixed by welding, gluing, clamping and/or screwing. Preferably, the means for connecting the first electrode are provided with the same material as a connected medical device. It is emphasized that the means for connecting the first electrode can be also provided by the means for holding the medical device. I.e. the means for holding the medical device and the means for connecting the medical device are provided by only one component. In one embodiment the means for connecting the first electrode are at least partially provided with a thread.

In a further embodiment means for adapting the electrical field are provided. For instance the means for adapting the electrical field are provided as a component to avoid edges and therefore to avoid regions of enhanced electrical field density. In one variant according to the invention the means for adapting the electrical field are embodied as a cap. This cap can be screwed on the thread.

In another embodiment a gas supply to the colloid-dispersed system is provided.

The antibacterial coatings according to the invention could be used in the field of traumatology, orthopaedic, osteosynthesis and/or endoprothesis, especially where high infection risk exists. A high number of currently existing implants or products could benefit from such a anti-bactericidal coating.

The medical device is a medical device which is at least partially inserted or positioned in a human body and/or an animal body. The medical device can be any kind of a medical device.

In one embodiment the medical device is an implant. The implant is a dental implant or an orthopaedic implant. Exemplary embodiments of such an implant according to the invention are plates, screws, nails, pins, and/or all, preferably external, fixation systems. It is emphasized that these applications are exemplary and not restricted to this enumeration.

In another embodiment the medical device is a medical instrument or tool. Exemplary embodiments of such a medical instrument are surgical instruments and/or diagnostic instruments. One example of a surgical instrument represents a scalpel. One example of a diagnostic instrument represents an endoscope. It is emphasized that these applications are exemplary and not restricted to this enumeration.

The surface converted implants according to the invention base in a preferred embodiment on biocompatible materials but preferably not on biodegradable materials. They are intended for long-term application, for instance for several days up to months, and/or for quasi-permanent application, as for instance for long term implantation of surgical implants and/or prothesises. However, the present invention is also applicable for biodegradable materials.

The implant comprises at least one metal selected from the group consisting of titanium, titanium alloys, chromium alloys, cobalt alloys and stainless steel. An alloy comprises at least 50 weight-% of the named main element. Some typical examples for titanium alloys are TiAl6V4, TiAl6Nb7 and/or TiZr. Some typical examples for chromium alloys are CrNi and/or CrNiMo. Some typical examples for cobalt alloys are CoCr and/or CoCrMo. Some typical examples for stainless steel are types 316L and/or 304. It is emphasized that above mentioned alloys are exemplary and not restricted to this enumeration.

In particular the apparatus according to the invention is adapted to execute any of the method steps according to the invention. In particular the method according to the present invention is feasible by means of the apparatus according to the invention. In particular the medical device, for instance an implant, according to the invention is producible, preferably is produced, by means of the apparatus according to the invention and/or with the method according to the invention. The or a medical device, for instance embodied as an implant, comprises a surface composed of an oxide film which is partially covered with islands of an antimicrobial material, preferably silver, and/or with an apatite, preferably HA.

The invention is explained subsequently in more detail on the basis of preferred embodiments and with reference to the appended figures. The features of the different embodiments are able to be combined with one another. Identical reference numerals in the figures denote identical or similar parts.

BRIEF DESCRIPTION OF THE DRAWINGS

It is shown in

FIGS. 2a to 10 show results of an Ag—TiO2 coating according to the invention.

In detail, it is shown in

Figure 2A:
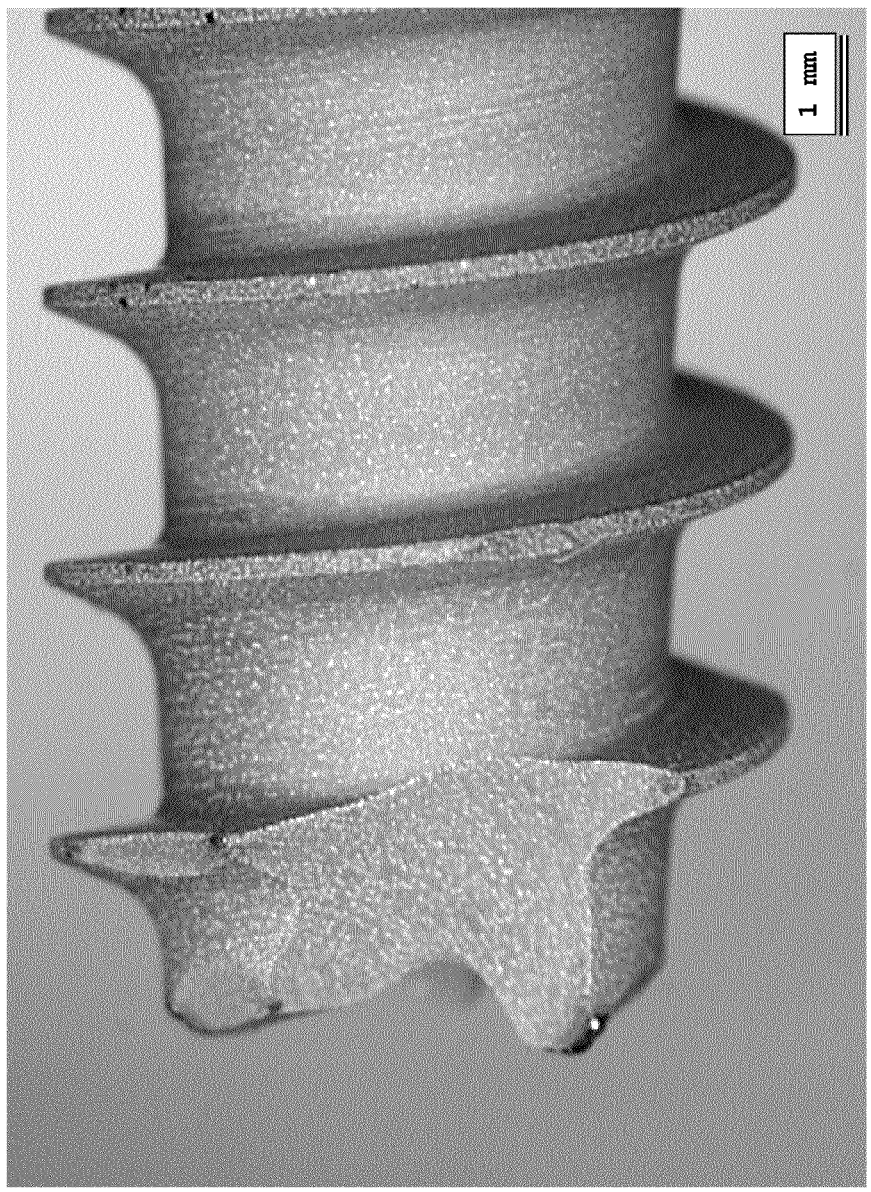
Figure 2B:
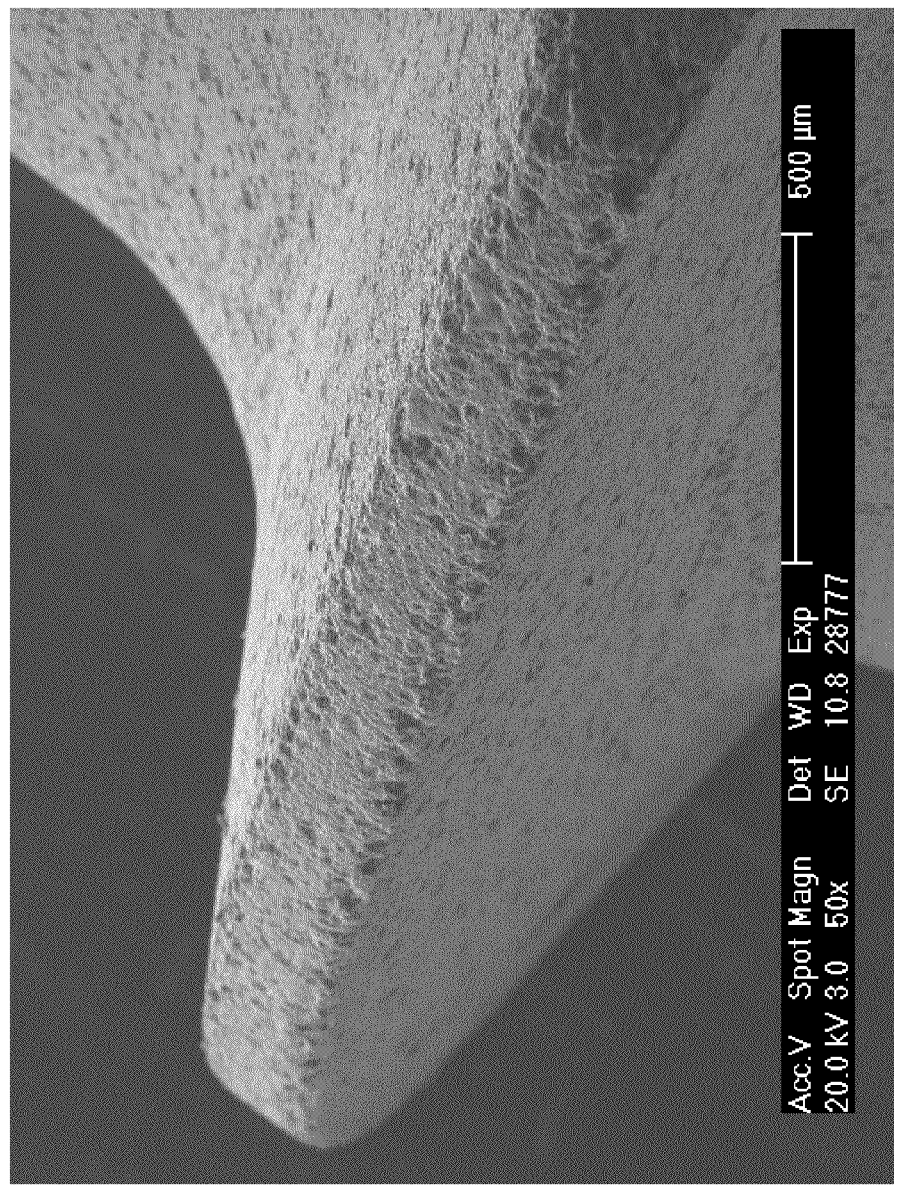
Figure 2C:
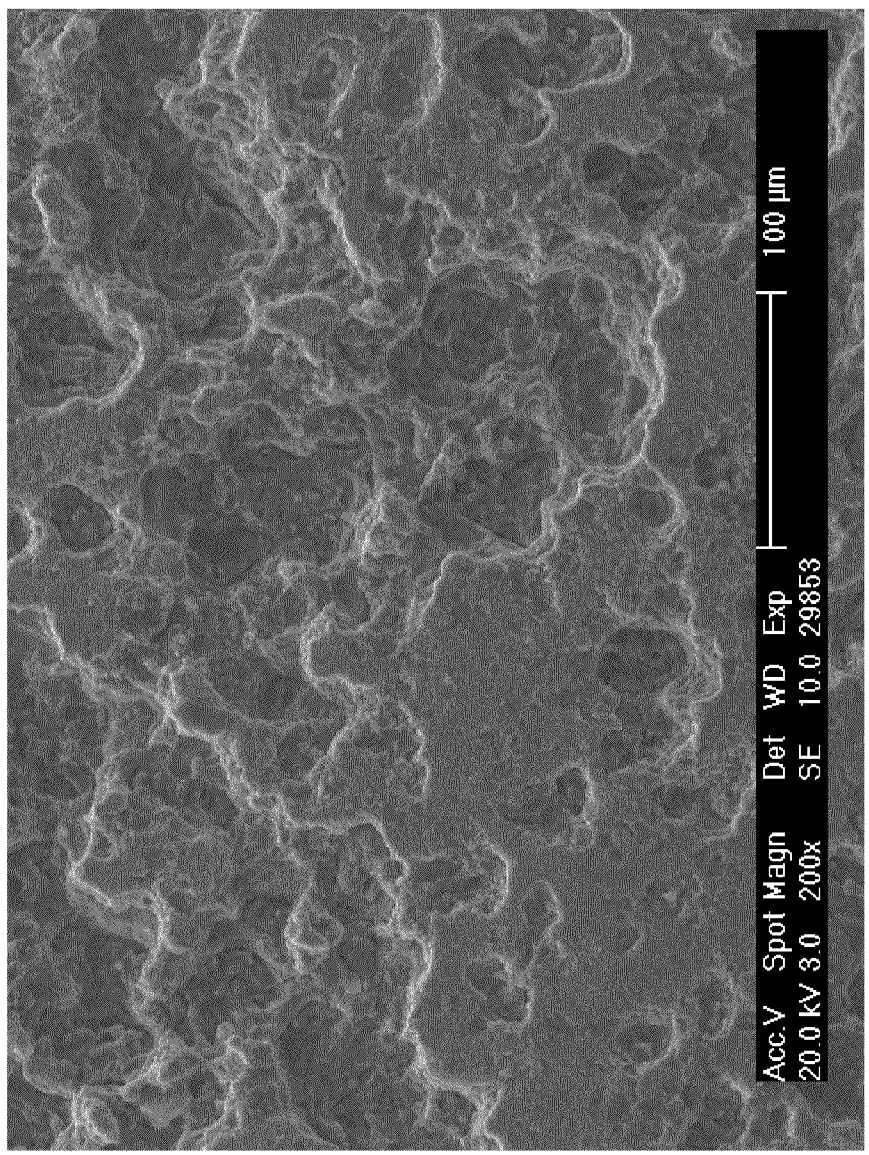
Figure 2D:
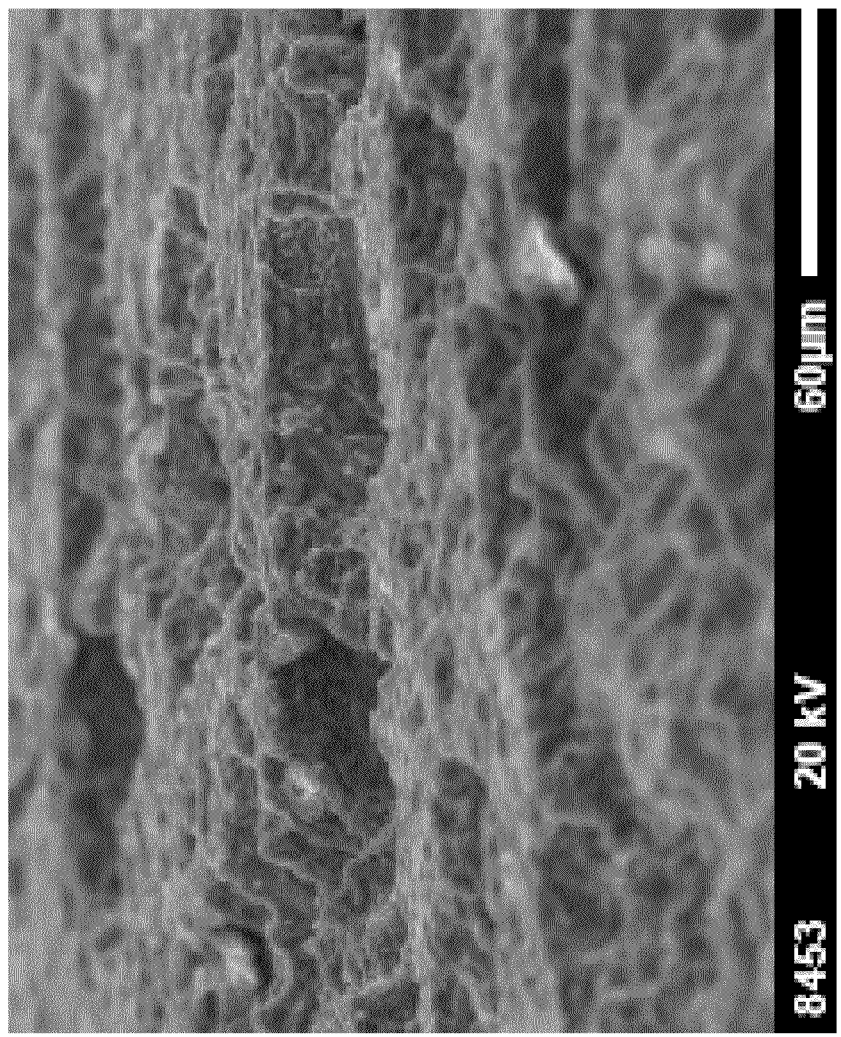
Figure 2E:
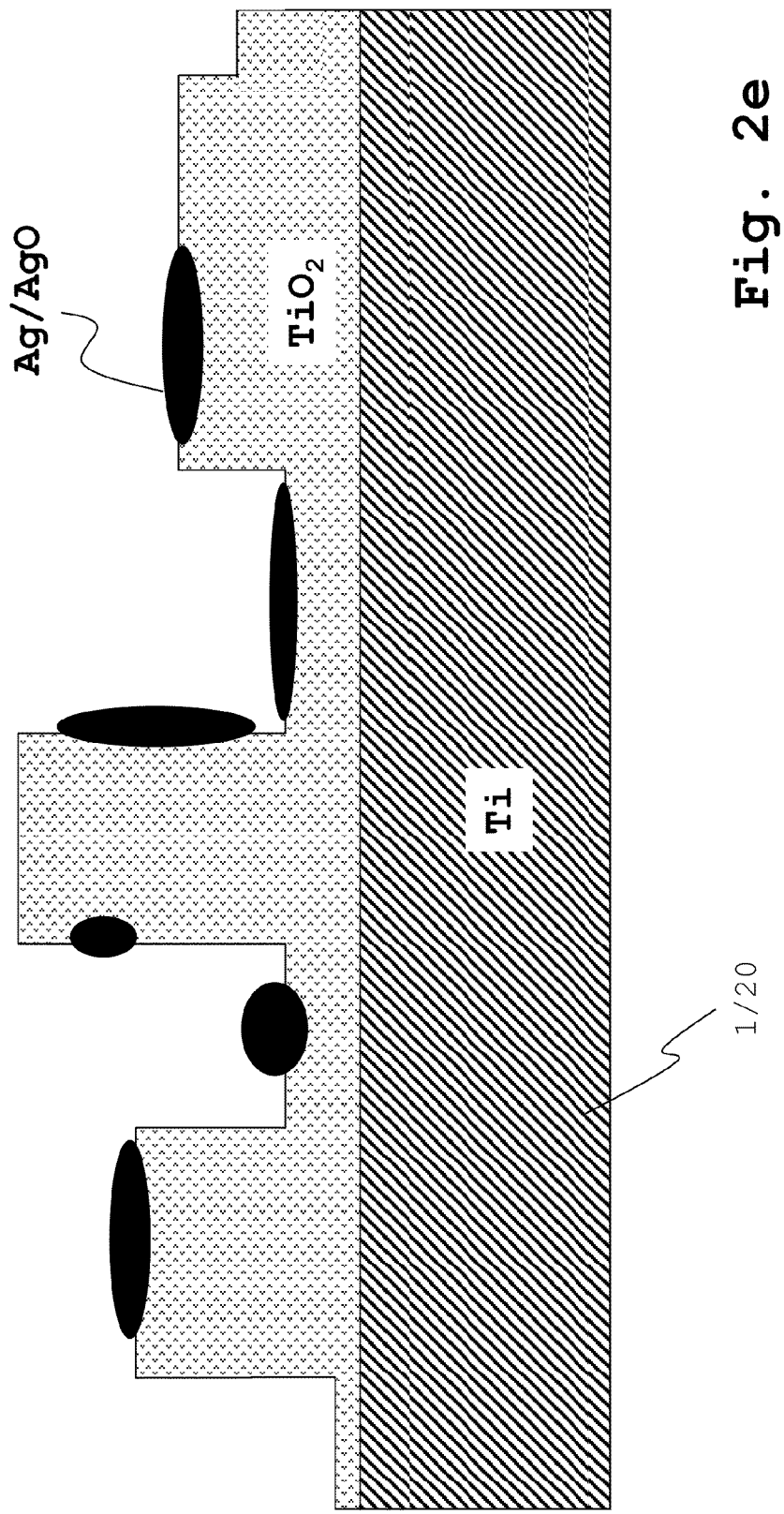
Figure 3A:
Figure 3B:
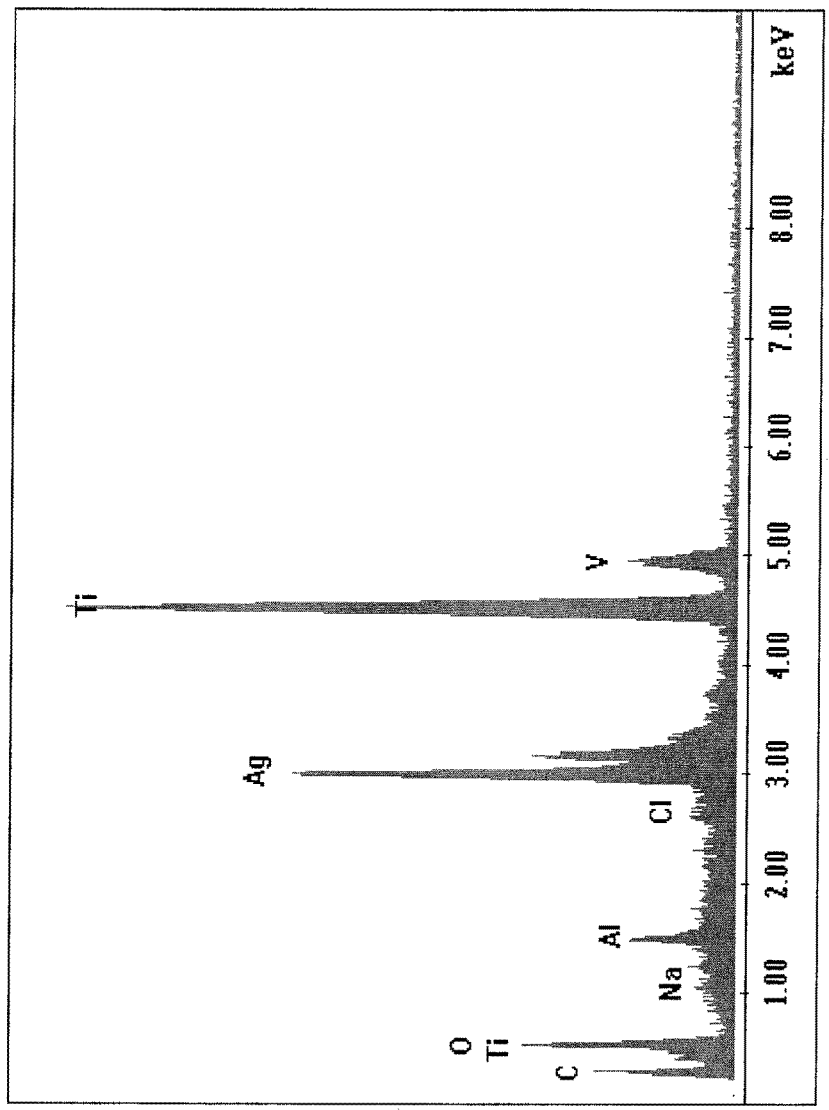

FIGS. 2a-e: images of the nanoSilver coating using Stereo Light Microscopy (a), SEM in topography contrast mode (b-c), tilted SEM in topography contrast mode (d), a schematic cross sectional view of the converted surface (e), FIGS. 3a-b: (a) an SEM image of the nanoSilver coating in chemical contrast mode, (b) an EDX spectra of the bright region, FIGS. 4a-b: XPS depth profile analysis of the nanoSilver coating, FIG. 5a: the method steps for the preparation of the biofilm test, FIG. 5b: bacteria amount found on the nanoSilver, Ag-rods and Ti-alloy rods after 12 h of incubation, FIGS. 6a-6e: the method steps for the preparation of the proliferation test (a), the interpretation of the growth curves (b-d), the achieved experimental results (e), FIG. 7: analytical results obtained by GF-AAS, in a pseudo-dynamic model, FIG. 8: analytical results obtained by GF-AAS, in a static model, FIGS. 9a-9b: Stereo Light Microscopy images of a coated rod after bending test, FIG. 10: SEM image of ZK20 cells on nanoSilver coating and FIG. 11: XRD image of a converted Ti-surface with a HA coating.

Subsequently, preferred but exemplar embodiments of the invention are described in more detail with regard to the figures.

DETAILED DESCRIPTION

FIG. 1 illustrates an apparatus for the fabrication of a coating according to the invention. The subsequent detailed description is only directed to an implant as one exemplary embodiment of a medical device. For instance for the coating of long term implantation surgical implants the present innovative technique based on the Plasma electrolytic oxidation (PEO) has been developed. PEO is an electrochemical surface treatment process for generating oxide coatings on metals. As a pulsed alternating current, with a high voltage, is passed through the colloid-dispersed system 4 or the electrolyte bath 4, a controlled plasma discharge is formed and sparks are generated on the substrate surface. This plasma discharge converts the surface of the metal into an oxide coating. The coating is in fact a chemical conversion of the substrate and grows both inwards and outwards from the original metal surface. Because it is a conversion coating, rather than a deposited coating (such as a coating formed by plasma spraying), it has excellent adhesion to the substrate metal (see FIGS. 9a and 9b). A wide range of substrate alloys can be coated with this technique.

The dispersed system 4 is provided in a bath 5. An implant 20 as a first electrode 1 is provided in the dispersed system 4. In the illustrated embodiment the implant 20 is completely immersed in the liquid 4 respectively the dispersed system 4. A second electrode 2 is provided as a cup also immersed or provided in the colloid-dispersed system 4. The second electrode 2 "surrounds" the first electrode 1.

The temperature of the dispersed system 4 is maintained or controlled by a heat exchanger 6 and/or a pumping system 7 and/or means for mixing 8. A circulation and/or mixing of the dispersed system 4 is achieved by the means for mixing 8. The means for mixing 8 are for instance provided by an acoustic hydrodynamic generator. As a possible and shown supplement a gas supply 9, for instance for air, can be also provided to the means for mixing 8. The circulation of the liquid avoids an agglomeration of the nano-particles contained in the dispersed system 4.

In a further non-shown embodiment the second electrode 2 is provided by the bath 5 or the container 5 itself. This is for instance suitable for a container 5 which is provided by a conductive material. In such an embodiment the bath 5 and the second electrode 2 are provided as one-piece.

In a preferred embodiment the first electrode 1 is approximately positioned in the center of the second electrode 2 to achieve a uniform electrical field distribution. The design of the means for connecting 3 the first electrode 1 is chosen to preserve an essential uniform or adapted electric field distribution between the first electrode 1 and the second electrode 2. For this the cross section and/or the geometry of the means for connecting 3 the implant 20 is/are adapted to the cross section and/or the geometry of the implant 20. FIGS. 1b to 1d schematically show three exemplary embodiments of the means for connecting 3 the implant 20.

FIGS. 1b to 1d illustrate possible embodiments of the means for connecting 3 each having an adapted reduced cross section with respect to the implant 20. Accordingly, the cross section ratio (representing the quotient of the medical device cross section divided by the cross section of the means for connecting the first electrode) is greater than 1 and less than 4. The reduced cross section of the means for connecting 3 is illustrated by the diameters d1 and d2 with d1<d2. The adapted reduced cross section is particularly determined in the vicinity or the area of the interface 35 between the implant 20 and the means for connecting 3.

In FIG. 1b the means for connecting 3 the first electrode 1 (respectively the implant 20) are embodied as a wire 3. The wire 3 is embodied as a, preferably cylindrical, rod 3. The rod 3 is embodied both for enabling the electrical contact and for holding the implant 20.

FIG. 1c illustrates the coating configuration for a nut as an implant 20. Since nuts 20 are generally quite small, for instance below or equal to 1 cm, the coating of a nut 20 is quite "complicated". The means for connecting 3 the first electrode 1 are also embodied as a wire 3. The wire 3 is partially embodied as a, preferably cylindrical, rod 3. The end-section of the rod 3 is embodied with a thread 31. The nut 20 is screwed on the thread 31. A cap 32 is applied or screwed to the end-section of the thread 31. The gaps above and below the nut 20 have a size of about 1 mm. The application of such a cap 32 enables the formation of a uniform coating also on the upper and the lower front side of the nut 20. The cap 32 represents means for adapting the electrical field. The rod 3 is embodied both for enabling the electrical contact and for holding the implant 20.

In FIG. 1d the means for connecting 3 the first electrode 1 (respectively the implant 20) are embodied as well as a wire 3. The wire 3 is now embodied as a strand 3. The strand 3 enables only the electrical contact. It is fed through a holder 33 which is preferably non-conductive. The holder 33 mechanically holds the implant 20.

Figure 1E:
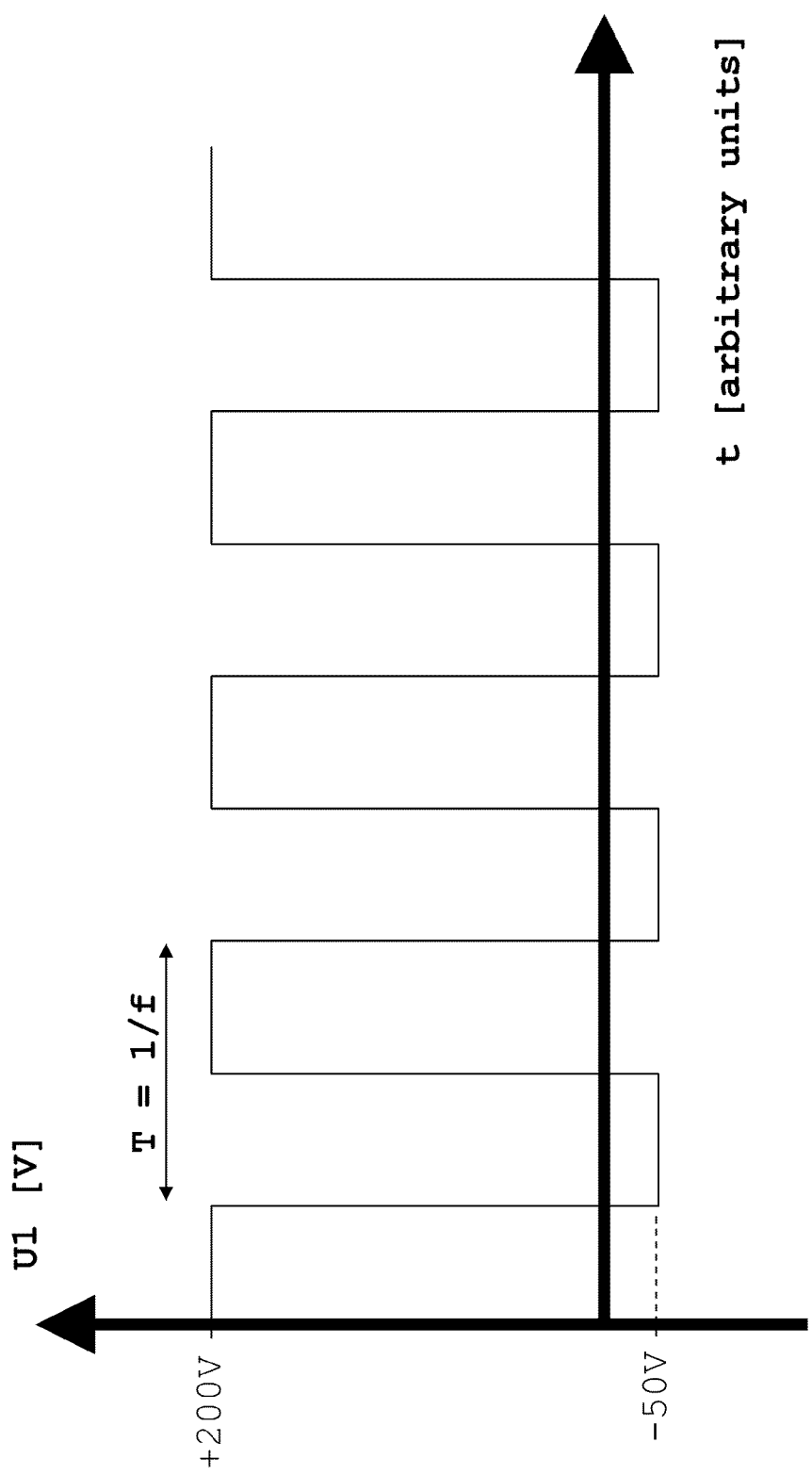
FIG. 1a schematically an apparatus for the fabrication of a coating according to the invention, FIG. 1b schematically a first embodiment of the means for electrically connecting the medical device, FIG. 1c schematically a second embodiment of the means for electrically connecting the medical device, FIG. 1d schematically a third embodiment of the means for electrically connecting the medical device, FIG. 1e schematically one embodiment of an asymmetric AC voltage distribution FIG. 1f schematically one embodiment of a symmetric AC voltage distribution

The AC voltage is provided by the power supply 10 (see FIG. 1a). The application of an asymmetric pulsed AC voltage results in a dense coating. The positive part of the pulse enables the growing of the converted surface. At the beginning of the oxide layer growing process the converted surface is characterized by a dense structure. With increasing oxide layer coating thickness the coating is getting more and more porous. The particles of the coating are getting more and more loosen. These loosen particles are removed in the negative part of the pulse. Accordingly, the negative part of the pulse is a so-called etching part. An asymmetric AC voltage is a voltage with different amplitudes to the positive and negative components. In particular the quotient of the positive amplitude divided by the negative amplitude needs to be adjusted. The absolute value of the quotient ranges from >1 to 4. For illustration purposes FIG. 1e schematically shows an asymmetric AC voltage distribution for amplitudes U1 of +200 V and −50V. These voltages are for instance applied to the implant 20 as the first electrode 1 (see FIG. 1a). In this embodiment the voltage of the second electrode 2 is for instance on ground potential. The shape is illustrated as being approximately rectangular-shaped. The shape can also be, in particular partially, a kind of a sinus or a sinus. For some applications also a symmetric AC voltage distribution is suitable. One exemplary application is the obtaining of a coating with a very high surface roughness for improved implant-bone bonding. For illustration purposes FIG. 1f schematically shows a symmetric AC voltage distribution for amplitudes U1 of −200 V and +200V.

Nanosilver particles with a particle size of about 1 to 20 nm, preferably 15 nm, are very suitable. This leads to an enhanced specific surface area and therefore to a high amount of dissolvable silver ions. The silver ions are responsible for the specific activity against a broad variety of bacteria, fungi and yeasts.

Silver ions inactivate critical physiological functions like cell-wall synthesis, trans-membrane transport, nucleic acid reproduction or protein functions. All of these actions result in a short-term death of microorganisms. Because of this multiple modes of antimicrobial action, it is very improbable, that the microorganisms develop a resistance to silver. Beyond the antimicrobial activity of the silver ions, new research projects show, that nanosilver in particular shows an activity against viruses like HIV or hepatitis.

FIGS. 2a to 11b show experimental results of an Ag—TiO$_2$ coating according to the invention. The used substrate or implant material is TiAl6V4 ELI alloy. TiAl6V4 ELI alloy (Extra Low Interstitials, ISO 5832-3) is a higher purity grade of TiAl6V4 alloy. This grade has lower oxygen, carbon, and iron content. It is commonly used in biomedical applications such as surgical instruments and orthopedic implants.

First, FIGS. 2a to 2d show the results of a topographical characterization (according to ISO/TS 10993-19:2006). As an example a screw having a coating according to the invention was analyzed. The coating surface topography has been investigated by stereo light microscopy (FIG. 2a) and scanning electron microscopy (SEM) in topography contrast mode (FIGS. 2b to 2d).

The images show a uniform and homogeneous coating of the surface (FIGS. 2a and 2b). At higher magnification the characteristic features of the PEO coatings are revealed: flat elevated plateaus with some deepening between them (FIG. 2c). The average deepening is 20 μm deep (FIG. 2d). The topographical characterization reveals a dense coating with a high specific surface area.

FIGS. 2c and 2d show the typical features of a converted surface by PEO. For illustration purposes FIG. 2e schematically shows a converted surface in a cross sectional view. The converted surface is continuously covered with the oxide layer. A typical thickness is below 25 μm. The oxide film is characterized by hills and/or plateaus separated by grooves and/or channels. On top of the oxide layer said islands are developed forming a non-continuous layer of metallic Ag and partially AgO. The islands can be formed on the plateaus and in the grooves. The islands have a typical thickness below 100 nm and a typical diameter ranging from 5 nm to 200 nm.

FIGS. 3a and 3b show the results of a physico-chemical characterization (according to ISO/TS 10993-19:2006). The SEM images in chemical contrast mode show the presence of a heavy element on the coating surface, in particular embodied as island (bright areas on FIG. 3b). Energy-dispersive spectrometry (EDS) confirms the presence of silver (FIG. 3a). Silver is homogeneously or uniformly distributed all over the coating surface. The typical silver-containing areas are much less than 1 μm.

Figure 4A:
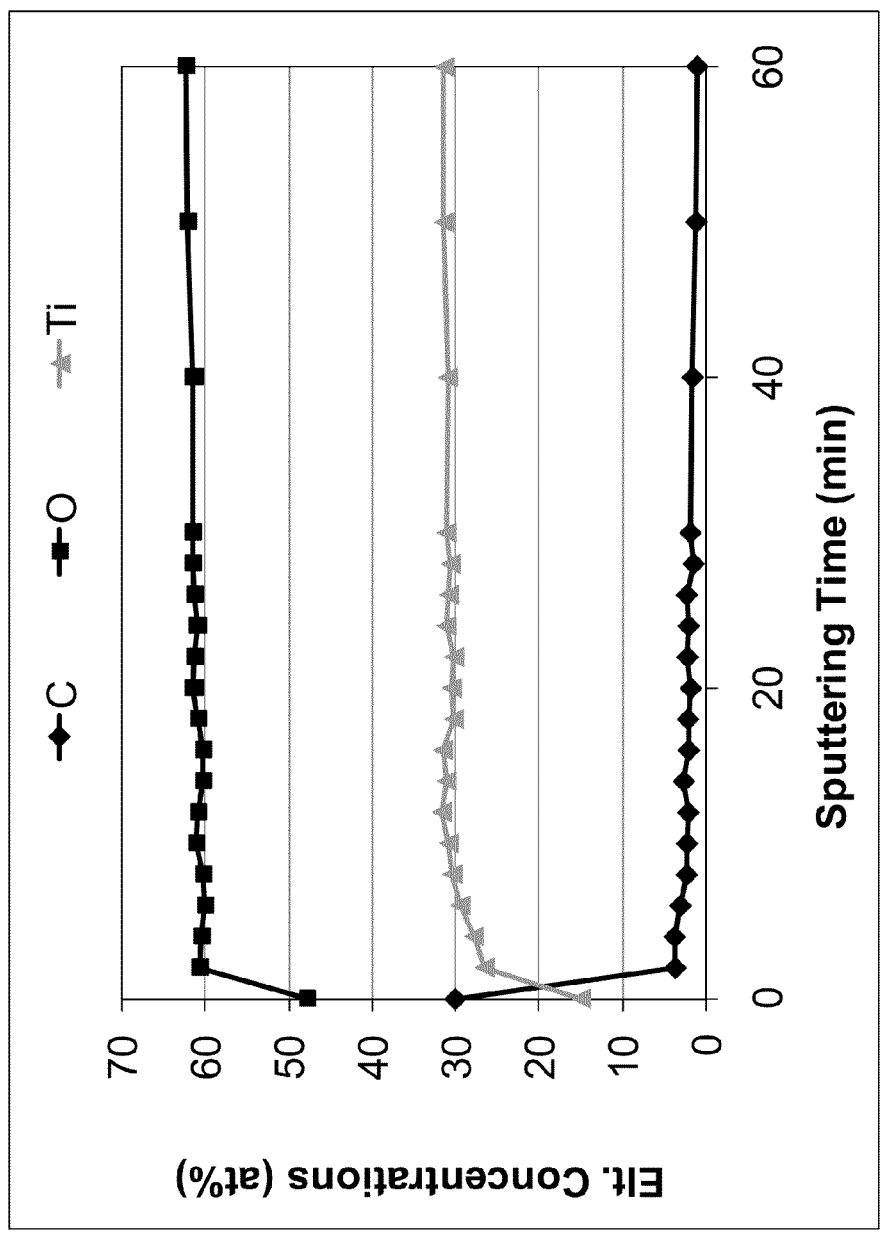
Figure 4B:
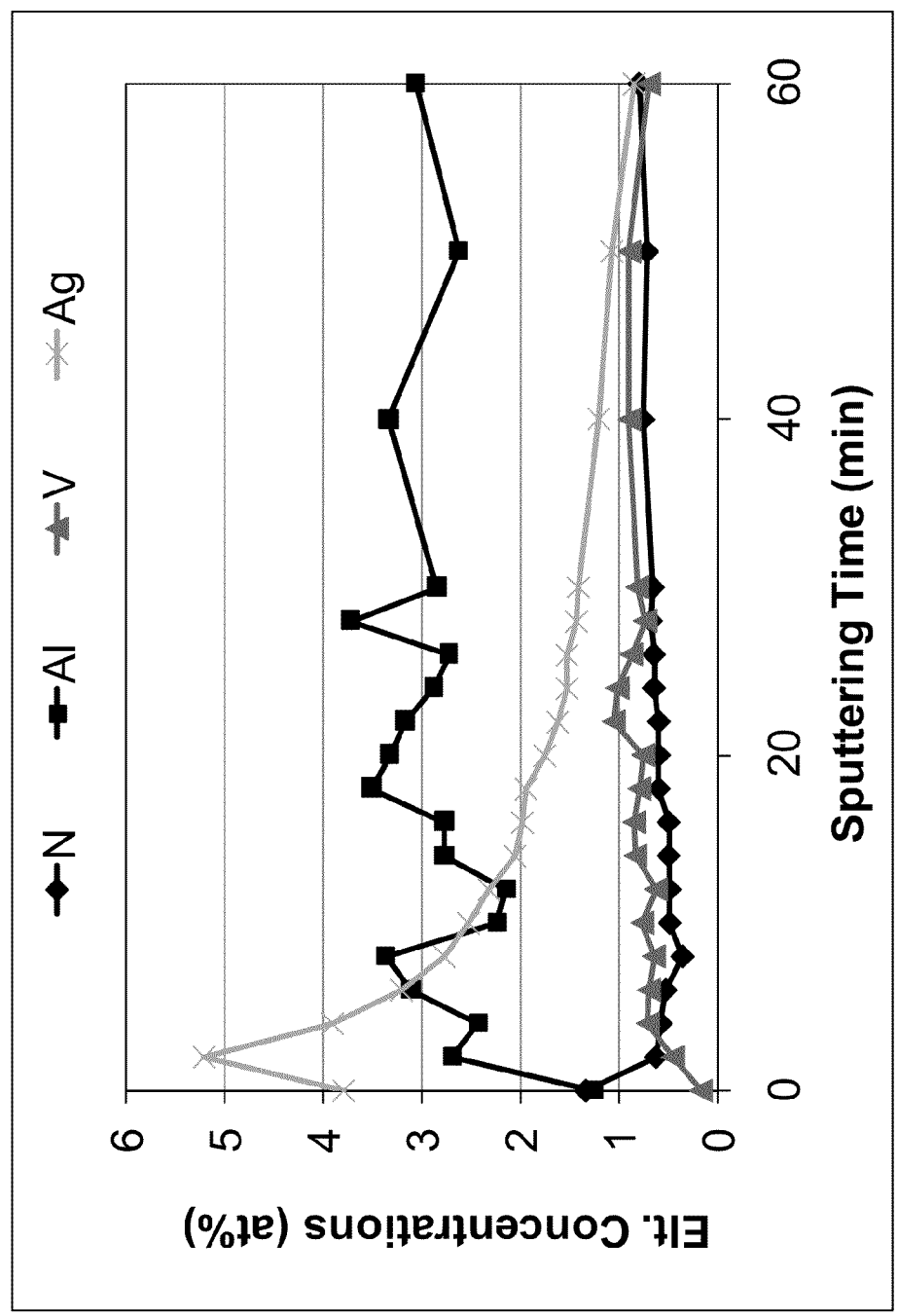

In FIGS. 4a and 4b results of a chemical characterization (according to ISO 10993-18:2005) are presented. The surface elemental composition was more precisely assessed by X-ray Photoelectron Spectroscopy (XPS) using a PHI 5500 ESCA spectrometer (monochromatic Al Kα radiation), each values reported below are the mean value of three independent analyses.

|  | Ag | Ti | Al | V | C | O | N | Cl | S |
|---|---|---|---|---|---|---|---|---|---|
| at. % | 3.6 | 14.7 | 1.2 | 0.3 | 30.3 | 47.7 | 1.4 | 0.5 | 0.3 |
| wt % | 16.8 | 30.4 | 1.4 | 0.7 | 15.7 | 33.0 | 0.8 | 0.8 | 0.4 |

The coating surface is mostly composed of titanium oxide with silver and carbon. Extremely low amount of nitrogen, chlorine and sulfur has also been found as contaminants.

XPS depth profiling (sputtering with a 3 keV Ar ions beam, surface area 3.8×4.2 mm) was performed on the coating to investigate its in-depth composition uniformity; an estimation of the thickness of the silver containing part of the coating was thus obtained: <100 nm.

After 2 min of sputtering the carbon content sharply decreases revealing the presence of a small organic surface contamination (FIG. 4a). This carbon surface contamination is often found by XPS and is probably due to the transport and the handling of the samples prior to the analysis. It's, also, after 2 min of sputtering that the highest concentration of Ag is detected (FIG. 4b).

Afterwards a continuous decrease of the Ag concentration is observed, revealing a diffusion pattern of the silver into the oxide layer. This observation is also consistent with the SEM results which indicate that the silver is present as small particles and not as a continuous layer. There is no sharp interface between the oxide layer and the Ag island. For instance, this is in contrast to surfaces converted to an oxide and deposited with an Ag coating.

High resolution binding spectra were also recorded (results are not shown). The 0 binding spectra refer mainly to TiO$_2$, with a small amount of other metal oxides (mainly Al and Ag). The Ag binding spectra shows the presence of silver oxides and metallic silver, no silver chloride was observed.

Subsequently are shown the results for the anti-microbial efficacy assessment of the coating according to the present invention. Materials for osteosynthesis (for instance pins, screws etc.) require for good biointegration a very specific surface, which allows human tissue cells to settle on them at the same time. This surface enables bacteria to settle, so that they compete with the human cells for proliferation on the surface.

The purpose of a nanoSilver-coating is the prevention of problematic bacterial growth on the surface of coated materials for osteosynthesis. One task of the invention is to find an optimal silver concentration for the coating, which shows a high antibacterial activity without any cytotoxic effect (according to ISO 10993-5).

The bacteria strain was used for every test: *Staphylococcus epidermidis* ATCC 35984.

This bacteria strain has the following characteristics:
Primary occupant of the skin.
Colonizes surfaces of prosthetic devices.
Biofilm formation ⇨ shield against the patient's immune system ⇨ use of antibiotics necessary.
Antibiotic resistant strains are spreading (actual rate of MRSE related to all *Staphylococcus epidermidis* strains in Germany: ca. 70%.).

No relevant standard has been found in common literature to assess the inhibition of a biofilm formation. Consequently a custom-made test was developed: The tests were performed using the *Staphylococcus epidermidis* ATCC 35984 strains. Pure silver rods were used as positive control and pure titanium alloy rods were used as negative control.

FIG. 5a illustrates the steps to prepare the samples and FIG. 5b shows the results of said biofilm formation test: The Bacteria amount found on the nanoSilver, Ag-rods and Ti-alloy rods depending on the incubation time. A sharp reduction of the bacteria amount has been observed on the Ag—$TiO_2$ coating compare to titanium-alloy (>log 3 reduction) after 12 h of incubation. The nanoSilver coating even shows better results than pure silver (FIG. 5b). After 18 h of incubation, no more bacteria were found on the surface of the Ag—$TiO_2$ coating. One explanation bases on an enhanced ratio of surface/volume of a nano-silver coating.

Figure 6A:
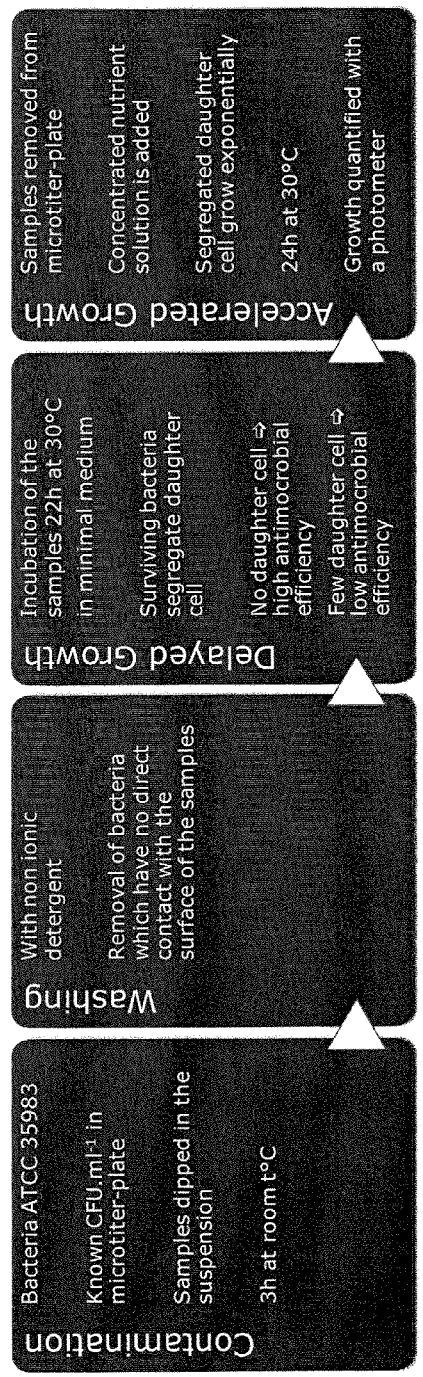

There exist several standard-test methods to determine the antimicrobial activity of coated surfaces. For screening purposes, a proliferation test is used. Bacteria commonly attend to adhere on surfaces. This ambition is mainly disturbed by antimicrobial and/or hydrophobic functionalization of surfaces, leading to a strong decrease in bacteria adhesion. The proliferation test shows this effect by the help of a specific test procedure. The bacterial growth behavior leads to an estimation of an antimicrobial effect on treated surfaces compared to an untreated surface. FIG. 6a shows the steps to perform the proliferation test.

The test is conducted with exponentially growing bacteria with commercially available 96-well-microtiter-plate. The test specimens ideally have a cylindrical shape with 4 mm diameter and a length of 12 mm.

The bacterial proliferation is determined by measuring the optical density at 578 nm in a special designed 64-fold-photometer.

Figure 6D:
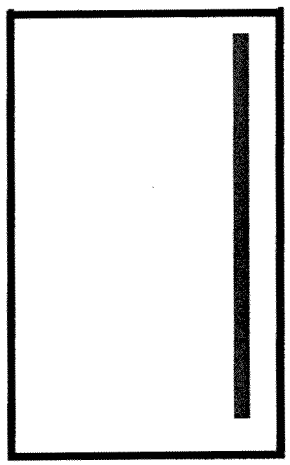
Figure 6C:
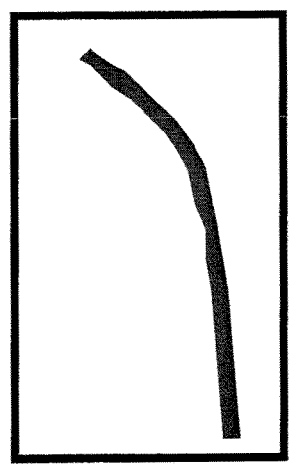
Figure 6B:
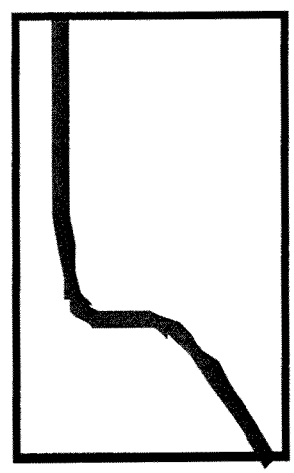
Figure 6E:
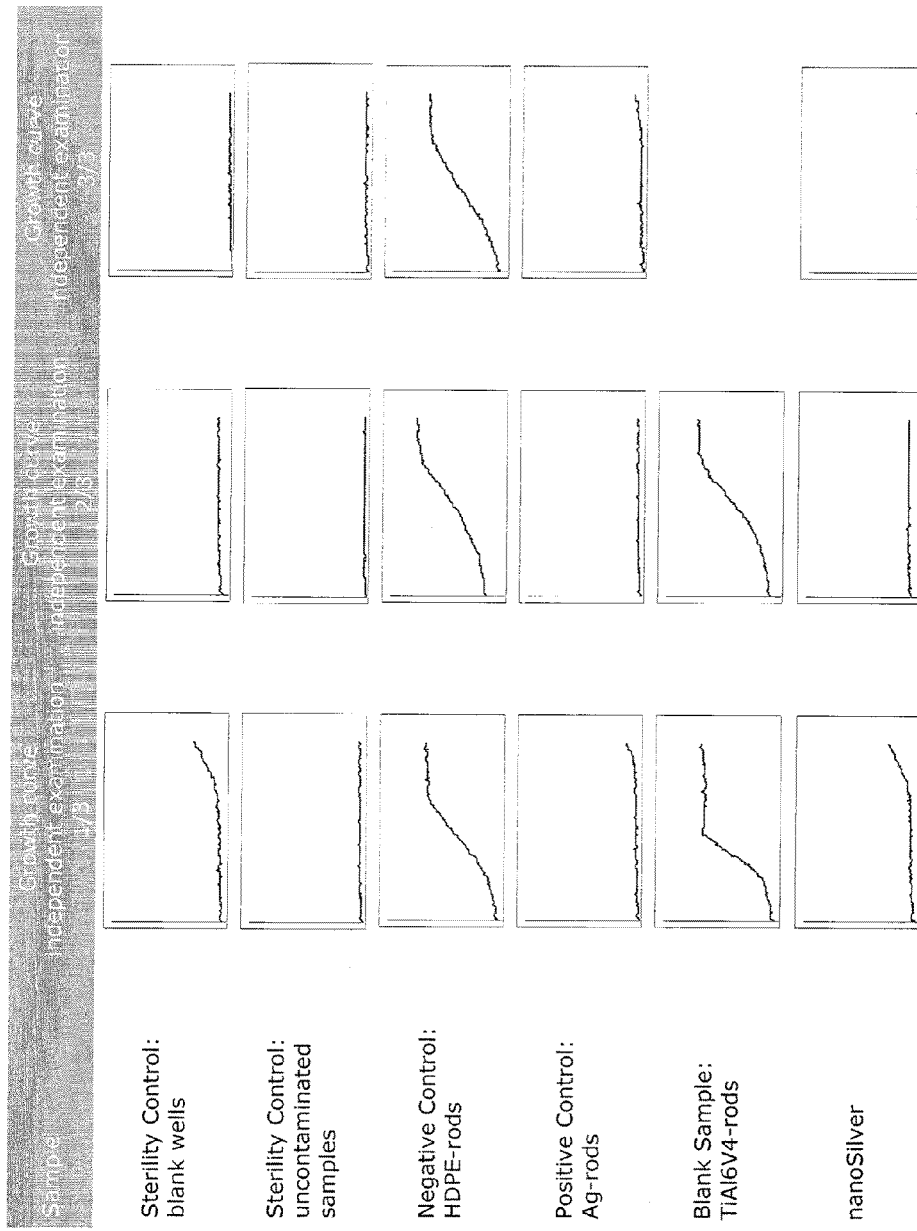

For each sample an individual growth curve is displayed (see FIG. 6e). The interpretation of the growth curves is illustrated in FIGS. 6b to 6d: (b) exponential growth—no antibacterial activity, (c) lag phase growth—slight antibacterial activity and (d) no detectable growth—strong antibacterial activity.

Samples (in each test round, internal controls were also tested):
Negative control: HDPE-rods (have to show exponential growth).
Medium growth control: Some wells of the microtiter-plate were filled up with contaminated nutrient solution to control the bacterial growth under optimal conditions.
Sterility control: blank wells and uncontaminated samples shall not show any bacterial growth.
Positive control: Pure Ag-rods (no growth should be detectable).

The antibacterial efficacy of the nanoSilver coating is estimated by comparing the bacterial growth on that surface with an untreated surface (Blank).

Blank samples: TiAl6V4 Eli Alloy rods.
Samples with nanoSilver coating: TiAl6V4 Eli Alloy rods with Ag—$TiO_2$ coating (5% recipe).

The results are presented in FIG. 6e. All controls show the expected growth curves, the test is valid. Compared to pure titanium rods, the Ag—$TiO_2$ coated rods show a strong antibacterial efficacy, which is as high as of pure silver rods.

A test for antimicrobial activity and efficacy is performed according to JIS 22801. The JIS Z 2801 standard specifies the testing methods to evaluate antimicrobial activity and antimicrobial efficacy on bacteria on the surface of antimicrobial products. The value of antimicrobial activity shows the difference in the logarithmic value of viable cell counts between antimicrobial products and untreated products after inoculation and incubation of bacteria. So in contrast to the Proliferation test the antibacterial activity can be quantified.

This testing method is applicable to products other than textile products, such as plastic products, metal products, and ceramic products.

The test samples were inoculated with a certain number of bacteria after preparation. To assure a good distribution of the inoculum, the test piece is covered with a special film (PE-foil). The test pieces are incubated at 37° C. for 18 h. After incubation, the bacteria were washed out with nutrient solution. With this washing suspension a viable cell count (agar plate culture method) is conducted.

Samples:
Blank sample: TiAl6V4 Eli Alloy disks.
Sample with nanoSilver coating: TiAl6V4 Eli Alloy disks with Ag—$TiO_2$ coating (5% recipe).
Negative control: Polystyrene-surface (a certain number of bacteria have to survive, otherwise the test has to be rejected).

The results show a strong antimicrobial activity of the nanoSilver, with more than log 4 reduction compared to TiAl6V4 Eli Alloy.

Further investigations were directed to silver leaching (according to ISO 10993-17:2002). The intention of this work package includes the correlation between antimicrobial activity and amount of released silver ions from the sample surface. It is developed a method of silver trace and species analysis with an appropriate method of sample preparation.

The analysis is performed by graphite furnace atomic absorption spectrometry (GF-AAS). The main focus has been laid on silver release mechanisms under physiological conditions. A test set up has to be created, which simulates conditions similar to the environment of the coating in a patients tissue. Therefore Phosphate Buffered Saline (PBS) was chosen as a leaching agent.

The Test Procedure is as Following:
Test Series A (Pseudo-Dynamic Model):
Samples are immersed in 1 ml PBS.
After 1 day gently shaking at 20° C. samples are transferred into the next vial with new PBS.
Test Series B (Static Model):
Samples are immersed in 10 ml PBS.
After certain intervals of gently shaking at 37° C. an aliquot (0.5 ml) is transferred into a fresh vial.
The Following Test Steps are Analogue in Both Test Series:
Ag content in PBS is analyzed after addition of nitric acid.
Silver analysis, done by graphite furnace atomic absorption spectrometry (GF-AAS).

Figure 7:
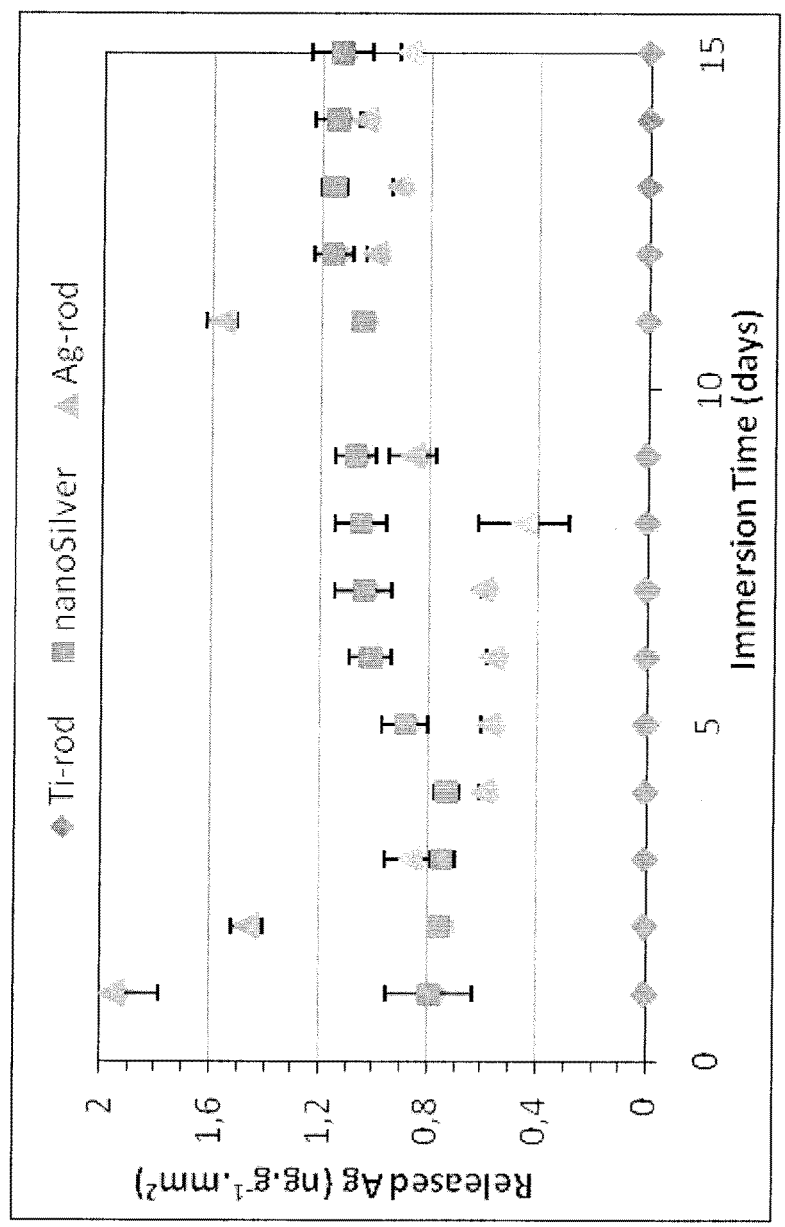

Tested Samples:
Blank samples: TiAl6V4 Eli Alloy rods (Ti rod).
Samples with nanoSilver coating: TiAl6V4 Eli Alloy rods with Ag—TiO$_2$ coating.
Positive control: pure silver rods (Ag rod)
The Following Results are Achieved:
Test series A: The nanoSilver coating shows silver release quite similar to pure silver rods.
FIG. 7 shows analytical results obtained by GF-AAS of released Ag amount (ng) from the sample surface (mm$^2$) as a function of immersion time (days) at RT in PBS. The displayed error bars show the variance of three independent analyses. The leaching rate is essentially uniform as a function of immersion time.
After 15 days:
Daily release from pure silver rod remains constant after a decrease in the first days.
Daily release from nanoSilver rod constant.
Sum of leached Ag amounts during 15 days of leaching: 6.3 μg.
The antibacterial activity (shown in the proliferation test) corresponds to the amount of released silver ions.
Test series B: According to our kinetics-test-conditions an equilibrium is reached after 24 hours.

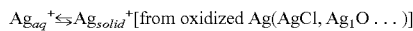

$$Ag_{aq}^+ \leftrightarrows Ag_{solid}^+ [\text{from oxidized Ag(AgCl, Ag}_1\text{O} \ldots )]$$

Figure 8:
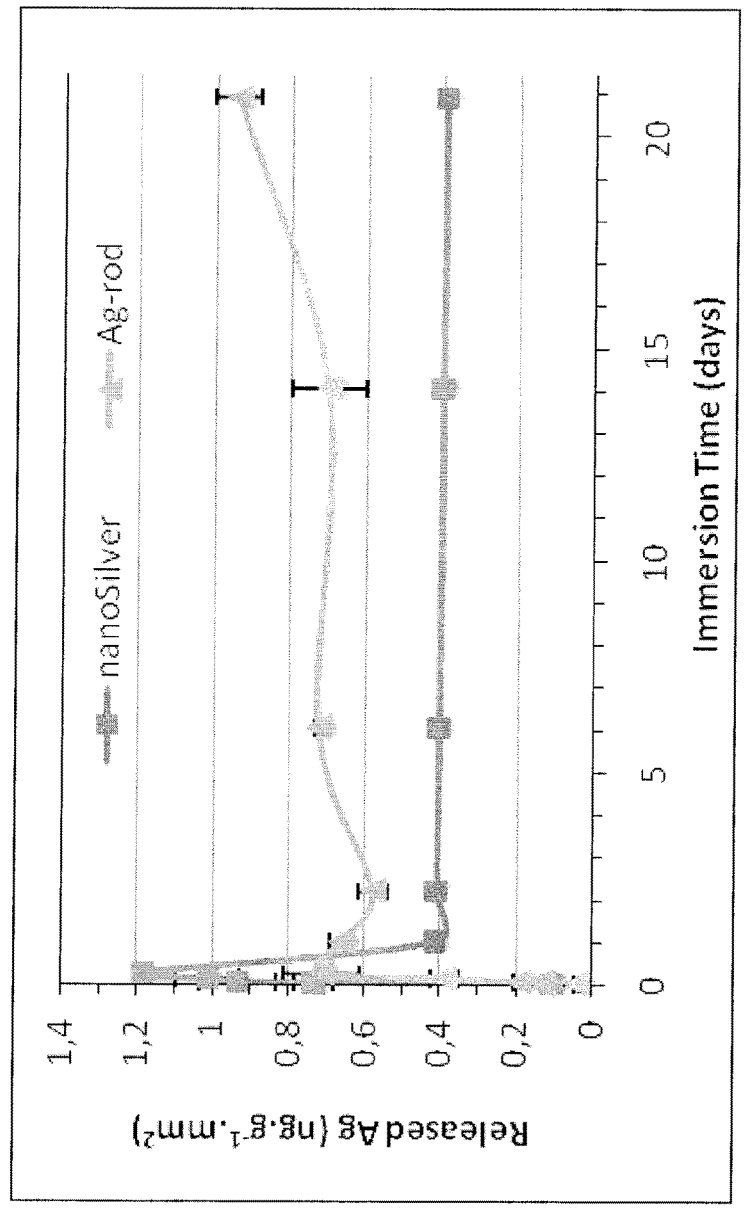
Figure 9B:
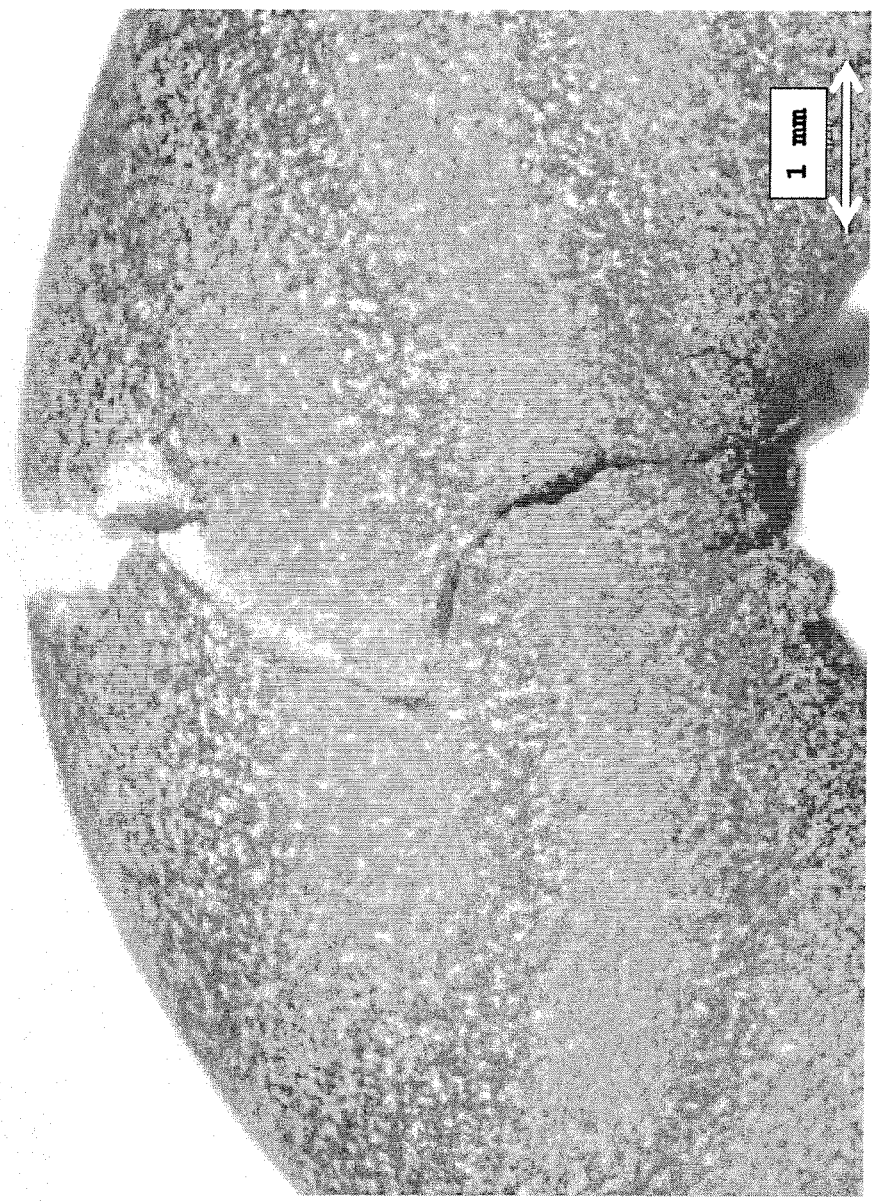
Figure 10:
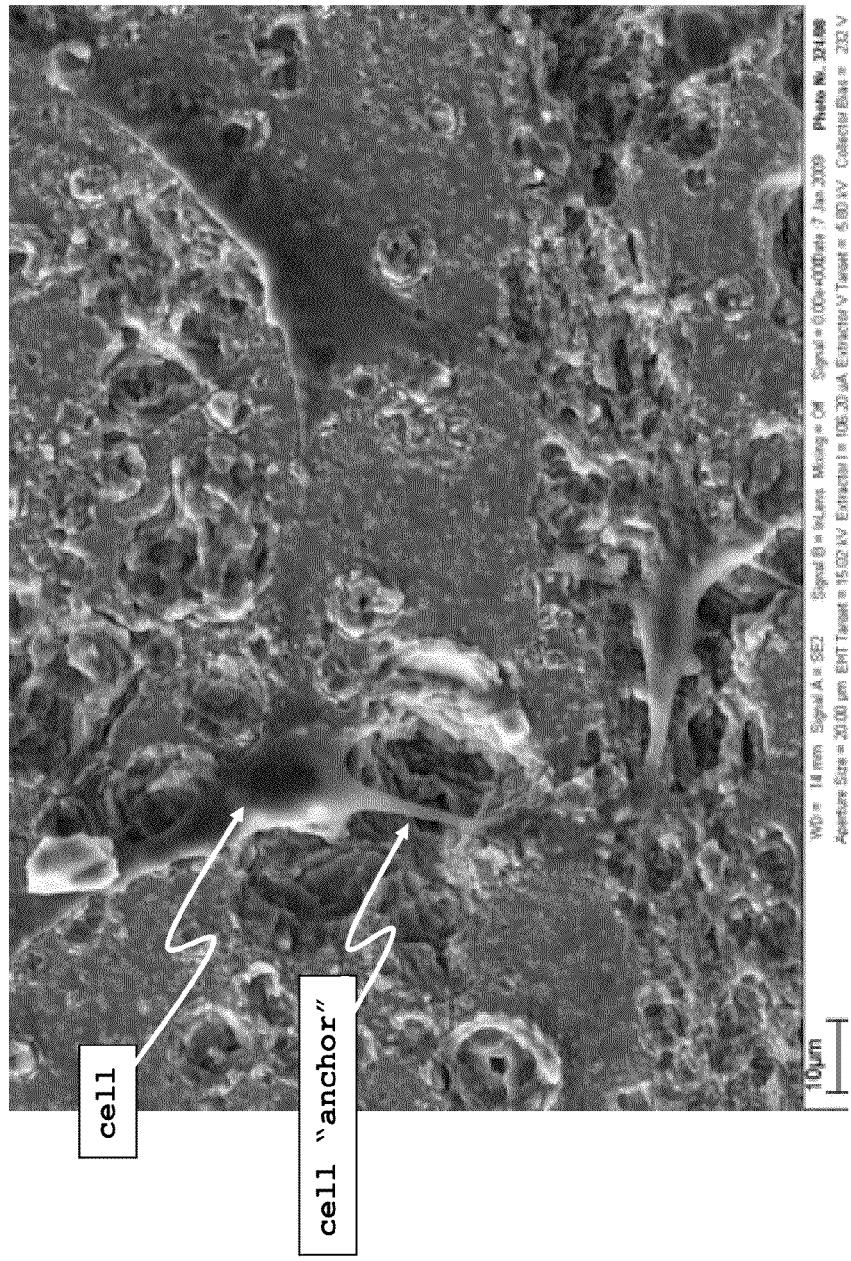
Figure 11:
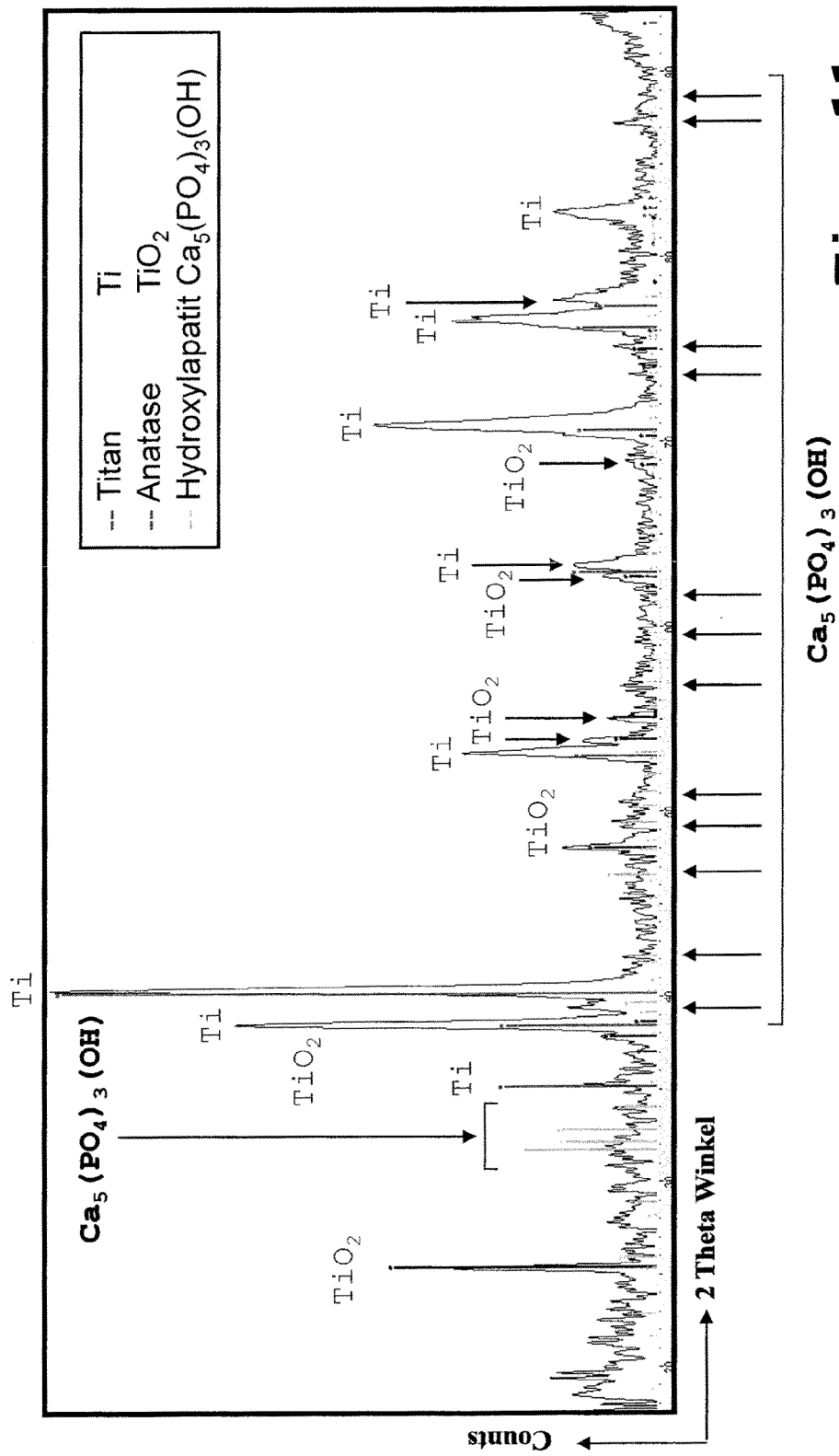

In this case the silver release at the equilibrium is about 0.4 ng·g$^{-1}$·mm$^{-2}$
If the 10 ml solution would be changed daily for 8 weeks, one can expect a total silver release of about 22.4 ng·g$^{-1}$·mm$^{-2}$.
FIG. 8 shows GF-AAS results of released Ag (ng) from the sample surface (mm$^2$) as a function of time (days) at 37° C. in PBS. The analytical data are a mean value of three independent analyses. The leaching rate is essentially uniform or constant as a function of immersion time.
FIGS. 9a and 9b show the results of a mechanical testing. Stereo light microscopy images of a coated rod after bending test are presented. The Ag—TiO$_2$ coating adhesion has been investigated according to the ASTM B571-97 standard. The coated samples have been bent at various angles and the deformed area has been observed by stereo light microscopy for any sign of peeling or flaking of the coating from the substrate. No peeling or flaking of the coating has been observed even after failure of the substrate has occurred. The adhesion strength of the coating is greater than the cohesion strength of the substrate, which reveals a perfect adhesion according to the used standard.
FIG. 10 shows the experimental results with respect to biocompatibility evaluation: ZK20 cells growing on nanoSilver/TiAl6V4 disks.
Cell culture has been performed using coated and uncoated TiAl6V4 disks as substrates. For this study two cell lines have been selected: the Osteosarcoma cell line (HOS TE85) and a primary mesenchymal stem cells from human bone dust (ZK20). The samples incubation has been performed at 37° C. in a 95% air-5% CO$_2$ atmosphere. After various incubation times (days or weeks, depending on the cell lines) the samples were prepared for light microscopy analysis and cells viability and proliferation have been investigated.
The two types of cell present a good adhesion and proliferation on the two types of surfaces (TiAl6V4 and nanoSilver). The two types of cell tend to agglomerate on the nanoSilver coating surface.
After a special fixation procedure, aimed at killing the cells with the least distortion of structure possible, the samples have been analyzed by electron microscopy. An SEM image of ZK20 cells on nanoSilver coating is presented. The SEM image confirms the good cell adhesion and proliferation on the nanoSilver coating surface. Even a kind of cell anchor is visible.
Summarizing, it was shown that an Ag—TiO$_2$ coating according to the invention shows excellent properties in terms of antibacterial efficacy (even against multi-resistant strains), adhesion and biocompatibility.
Finally, FIG. 11 presents a XRD image of a Ti-screw with a HA coating (hydroxyapatite). In detail it is presented the detected number of counts as a function of the angle 2 theta.
The parameters for this analysis are as follows:
Apparatus: Bruker D8 GADDS XRD (voltage: 40 KV and intensity: 40 mA)
Measurement range: Theta angle: 17-93.7° increment: 0.02° and steptime: 60 s
Measuring point: Top of the titanium screw.
The sample contains mostly Titanium and Anatase (TiO$_2$). Titanium and TiO$_2$ originate from the bulk respectively the converted surface. Also a very small quantity of HA is detected. The intensity differences of certain HA peak is due to a preferential orientation of the crystallites on the surface of the screw. However, these are the first hints that it is possible to detect HA itself on the converted surface and not only constituents of HA.
The small amount of detected HA can be explained by the selected configuration of the experimental set-up. The chosen angular range of the analysis beam results in an enhanced sensitivity to the bulk material (Ti) covered with a layer of TiO$_2$ (thickness of several μm) and to a reduced sensitivity to a surface and a near surface composition of HA (thickness of some 100 nm or below).
It is expected to detect an increasing amount of HA in a so-called grazing incidence geometry. In this geometry the analysis beam is directed to the surface in a small angle (for instance of about 1.5 degree) with respect to the surface which is to be analyzed. The sensitivity for the surface composition and the near surface composition is enhanced in this grazing incidence geometry.
It will be understood that the invention may be embodied in other specific forms without departing from the spirit or central characteristics thereof. The present examples and embodiments, therefore, are to be considered in all respects as illustrative and not restrictive, and the invention is not to be limited to the details given herein. Accordingly, features of the above described specific embodiments can be combined with one another. Further, features described in the summary of the invention can be combined with one another. Furthermore, features of the above described specific embodiments and features described in the summary of the invention can be combined with one another

The invention claimed is:
1. A medical device comprising a non-biodegradable metal or metal alloy having a treated surface
wherein the treated surface is at least partially converted to an oxide film by plasma electrolytic oxidation using a colloid-dispersed system, wherein colloid-dispersed particles of the colloid-dispersed system are provided by silver particles, and
wherein the converted surface is partially covered by islands formed by said silver particles
such that the converted surface is continuously covered with the oxide film which is characterized by plateaus separated by grooves,
wherein on top of the oxide film said islands form a non-continuous layer of metallic silver and partially silver oxide, with the islands being formed on the plateaus and in the grooves and with the islands having a thickness below 100 nm and a diameter ranging from 5 nm to 200 nm, wherein silver is homogeneously distributed all over the coating surface being present as particles with a particle size of about 1 to 20 nm.

2. The medical device according to claim 1 wherein the colloid-dispersed particles further comprise at least one member of a group consisting of, Cu-particles, Zn-particles, a component which is at least one component of a material of the medical device, and apatite-particles.

3. The medical device according to claim 1 wherein the colloid-dispersed particles comprise an additive wherein the additive is at least one material selected from a group consisting of metals, oxides, earth minerals and phosphates.

4. The medical device according to claim 1 wherein the oxide film has thickness of 1 µm to 100 µm.

5. The medical device according to claim 1 wherein the treated surface has an average island cover amount of less than 20%.

6. The medical device according to claim 1 wherein the treated surface has an Ag leaching rate of less than 120 $ng \cdot cm^{-2} \cdot day^{-1}$.

7. The medical device according to claim 1 wherein the non-biodegradable metal or metal alloy comprises at least one metal selected from the group consisting of titanium, titanium alloys, chromium alloys, cobalt alloys and stainless steel.

\* \* \* \* \*